US007101359B2

(12) United States Patent
Kline et al.

(10) Patent No.: US 7,101,359 B2
(45) Date of Patent: *Sep. 5, 2006

(54) ABSORBENT ARTICLE FASTENING DEVICE

(75) Inventors: Mark James Kline, Okeana, OH (US); Tracey Elaine Beckman, Milford, OH (US); Thomas Henrich, Cincinnati, OH (US); David Joseph Kenneth Goulait, West Chester, OH (US); Miguel Alvaro Robles, Cincinnati, OH (US); Constance Lee Fisher, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/125,895

(22) Filed: May 10, 2005

(65) Prior Publication Data

US 2005/0234419 A1  Oct. 20, 2005

Related U.S. Application Data

(63) Continuation of application No. 10/177,949, filed on Jun. 21, 2002, now Pat. No. 6,936,039, which is a continuation of application No. 09/143,184, filed on Aug. 28, 1998, now Pat. No. 6,432,098.

(60) Provisional application No. 60/057,613, filed on Sep. 4, 1997.

(51) Int. Cl.
*A61F 13/15* (2006.01)
*A41B 13/04* (2006.01)

(52) U.S. Cl. ............... 604/387; 604/392; 604/386; 604/385.03; 24/522; 24/610; 24/615

(58) Field of Classification Search .......... 604/387, 604/385.01, 385.03, 386, 396, 391, 392, 604/385.21, 385.23; 24/522, 580, 581, 610, 24/615, 431, 578.1, 578.11, 580.1
See application file for complete search history.

(56) References Cited

U.S. PATENT DOCUMENTS

| 198,097 | A | 12/1877 | Fries |
| 207,253 | A | 8/1878 | Chipley |
| 378,874 | A | 3/1888 | Davis |
| 771,719 | A | 10/1904 | Copeland |
| 779,279 | A | 1/1905 | Hastings |
| 791,654 | A | 6/1905 | Searle |
| 1,322,276 | A | 11/1919 | Wolff |

(Continued)

FOREIGN PATENT DOCUMENTS

CA        2023577        2/1992

(Continued)

*Primary Examiner*—Jacqueline F. Stephens
(74) *Attorney, Agent, or Firm*—Adam J. Forman; Jack L. Oney, Jr.; Ken K Patel

(57) ABSTRACT

A strong, easy to use tab and slot fastening device suitable for use with disposable absorbent articles. The fastening device preferably includes a tab member and a slot member. The slot member has an inboard portion, an outboard portion and a slot. The inboard portion located laterally inboard of the outboard portion and the slot located between the inboard portion and the outboard portion. The tab member has a length, a proximal edge, a distal edge and a lip portion. The tab portion is passed through the slot of the slot member to engage the fastening device. Once passed through the slot, at least the lip portion of the tab member pivots such that it overlaps the outboard portion of the slot member to prevent the tab member from disengaging from the slot member.

20 Claims, 15 Drawing Sheets

U.S. PATENT DOCUMENTS

| | | |
|---|---|---|
| 1,392,776 A | 10/1921 | Lindquist |
| 1,450,755 A | 4/1923 | Rider |
| 1,669,188 A | 5/1928 | Condylis |
| 1,800,739 A | 4/1931 | Marinsky |
| 1,824,556 A | 9/1931 | Lapworth |
| 2,019,835 A | 11/1935 | Voss |
| 2,049,913 A | 8/1936 | Lesueur |
| 2,094,292 A | 9/1937 | Cousens |
| 2,101,453 A | 12/1937 | Rhodes |
| 2,294,617 A | 9/1942 | Horowitz |
| 2,530,046 A | 11/1950 | Crossingham |
| 2,541,629 A | 2/1951 | Woods |
| 2,563,232 A | 8/1951 | GeJac |
| 2,570,796 A | 10/1951 | Gross |
| 2,611,364 A | 9/1952 | Mann |
| 2,629,380 A | 2/1953 | Schweikert |
| 2,837,096 A | 6/1958 | Leveillee |
| 2,931,361 A | 4/1960 | Sostrin |
| 3,288,141 A | 11/1966 | Mathison et al. |
| 3,335,721 A | 8/1967 | Gastwirth |
| 3,424,160 A | 1/1969 | Koornwinder et al. |
| 3,441,025 A | 4/1969 | Ralph |
| 3,482,289 A | 12/1969 | Stradella |
| 3,494,361 A | 2/1970 | Thivat |
| 3,575,171 A | 4/1971 | Rugen |
| 3,620,180 A | 11/1971 | Waldes |
| 3,635,221 A | 1/1972 | Champaigne, Jr. |
| 3,828,786 A | 8/1974 | Cervantes |
| 3,834,824 A | 9/1974 | Jahn |
| 3,921,639 A | 11/1975 | Cepuritis |
| 4,001,924 A | 1/1977 | Bengtsson |
| 4,014,340 A | 3/1977 | Cheslow |
| 4,182,334 A | 1/1980 | Johnson |
| 4,315,508 A | 2/1982 | Bolick |
| 4,555,244 A | 11/1985 | Buell |
| 4,608,047 A | 8/1986 | Mattingly |
| 4,701,170 A | 10/1987 | Wilson et al. |
| 4,701,176 A | 10/1987 | Wilson et al. |
| 4,701,179 A | 10/1987 | Kellenberger et al. |
| 4,704,114 A | 11/1987 | Wilson et al. |
| 4,728,326 A | 3/1988 | Gilles |
| 4,756,709 A | 7/1988 | Stevens |
| 4,838,886 A | 6/1989 | Kent |
| 5,135,522 A | 8/1992 | Fahrenkrug et al. |
| 5,176,671 A | 1/1993 | Roessler et al. |
| 5,207,665 A | 5/1993 | Davis et al. |
| 5,318,555 A | 6/1994 | Siebers et al. |
| 5,368,585 A | 11/1994 | Dokken |
| 5,374,262 A | 12/1994 | Keuhn, Jr. et al. |
| 5,395,355 A | 3/1995 | Wadman |
| 5,403,302 A | 4/1995 | Roessler et al. |
| 5,423,789 A | 6/1995 | Kuen |
| 5,656,111 A | 8/1997 | Dilnik et al. |
| 5,660,666 A | 8/1997 | Dilnik et al. |
| 5,704,933 A | 1/1998 | Fell et al. |
| 5,899,896 A | 5/1999 | Suprise et al. |
| 5,901,419 A | 5/1999 | Widlund et al. |
| 5,984,911 A | 11/1999 | Siebers et al. |
| 6,123,695 A | 9/2000 | Skog et al. |
| 6,290,687 B1 | 9/2001 | Skog et al. |
| 6,296,629 B1 | 10/2001 | Siebers et al. |
| 6,406,467 B1 | 6/2002 | Dilnik et al. |
| 6,406,468 B1 | 6/2002 | Dilnik et al. |
| 6,585,713 B1 | 7/2003 | Lemahieu et al. |
| 6,627,289 B1 | 9/2003 | Dilnik et al. |

FOREIGN PATENT DOCUMENTS

| | | |
|---|---|---|
| CN | 2192312 Y | 3/1995 |
| GB | 430131 | 6/1935 |
| GB | 493819 | 10/1938 |

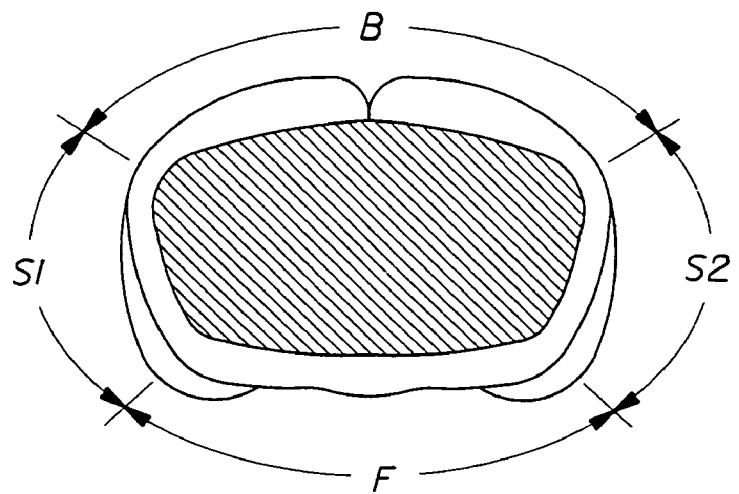
Fig. 20A
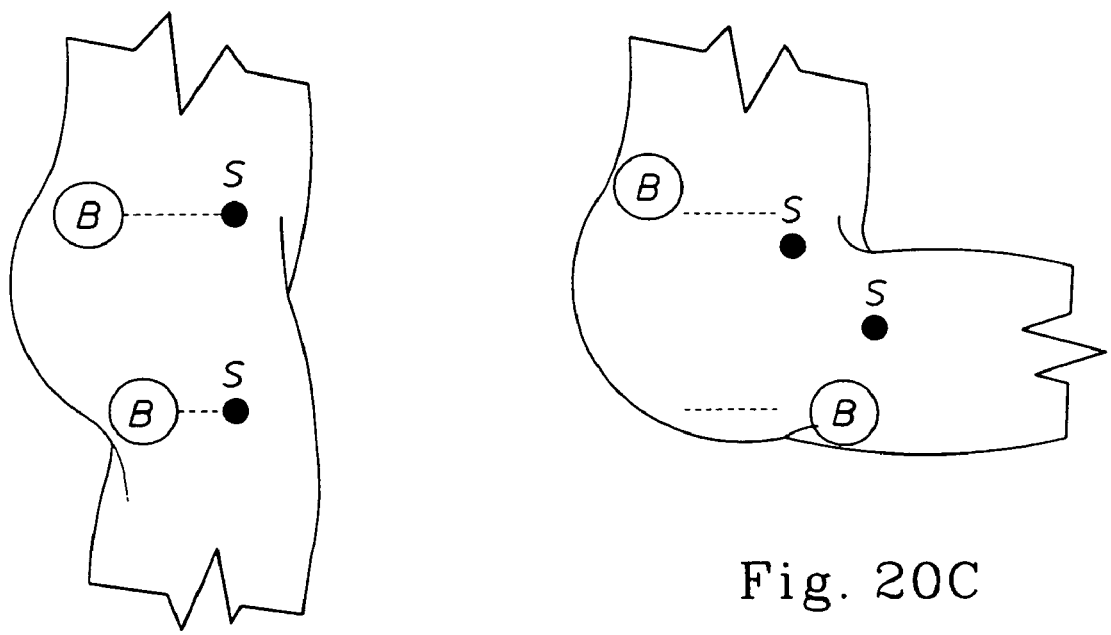
Fig. 20B
Fig. 20C

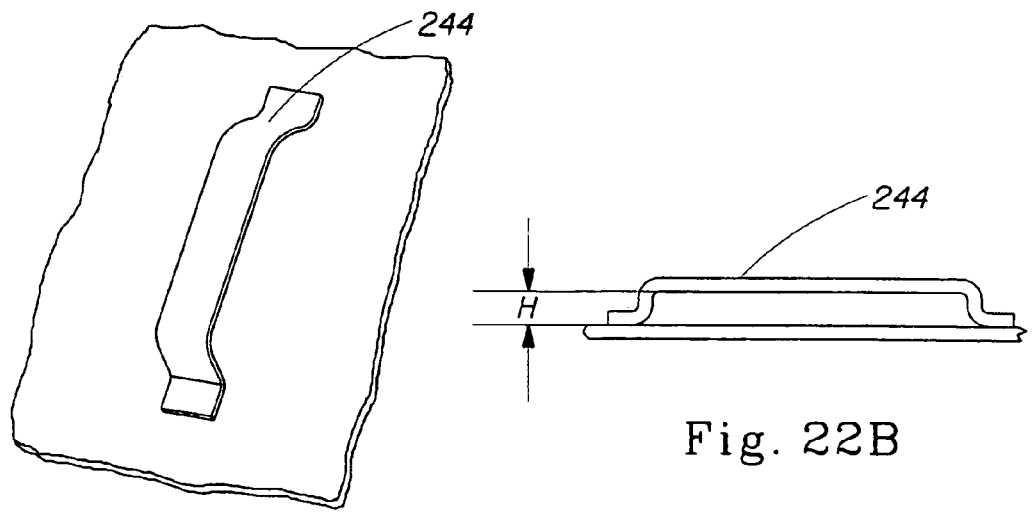
Fig. 22A
Fig. 22B
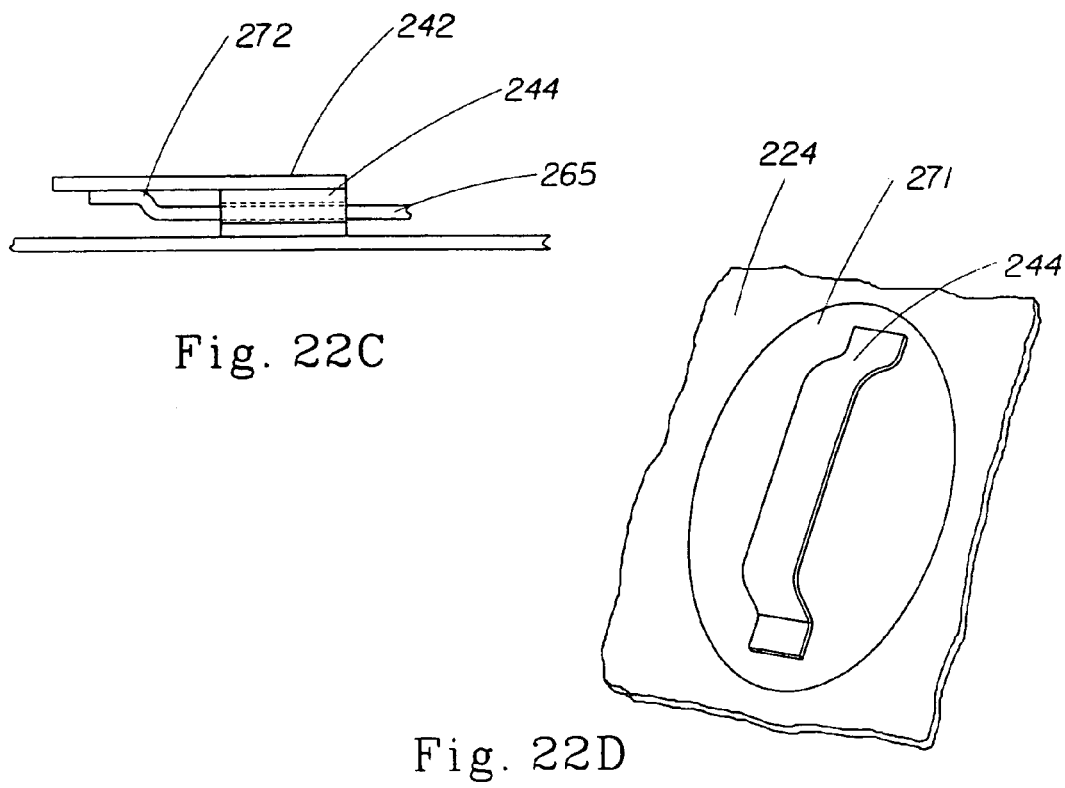
Fig. 22C
Fig. 22D

ABSORBENT ARTICLE FASTENING DEVICE

CROSS REFERENCE TO RELATED APPLICATIONS

This application is a continuation application of U.S. application Ser. No. 10/177,949, filed Jun. 21, 2002 now U.S. Pat. No. 6,936,039, which is a continuation application of U.S. application Ser. No. 09/143,184, filed Aug. 28, 1998, now U.S. Pat. No. 6,432,098, which claims priority to U.S. Application Ser. No. 60/057,613, filed Sep. 4, 1997.

FIELD OF THE INVENTION

The present invention relates to absorbent articles such diapers, training pants and incontinence pads. More particularly, the present invention relates to disposable absorbent articles having improved fasteners for joining the front of the article to the rear of the article and/or to provide for disposal.

BACKGROUND OF THE INVENTION

Many different types of refastenable fastening devices are known, including ties, pins, hook and loop systems, hook and eye systems, buttons, snaps, interlocking shapes, buckles, adhesive tapes, cohesive surfaces, and zippers and other slide connectors. Such fasteners have been used on a variety of products, both durable and disposable. Typical uses include envelopes, clothing, diapers, packages, footwear, construction closures, general attachment needs and feminine hygiene products.

Some fastening devices, such as hook and loop or adhesive tapes, require aligning an engaging surface with a landing surface. While this can result in an effective closure, it often results in misapplication and/or poor alignment of the elements being connected. Further, hook and loop fasteners can become ineffective due to compression and contamination or can harm surrounding materials. With an adhesive system, improperly fastening the device may render the entire product unusable. For example, in diaper applications, repositioning a tape tab which has been fastened improperly may result in tearing the outer cover of the diaper. Further, adhesive systems are prone to contamination-induced performance problems. In order to help prevent such problems, the use of these types of fasteners often require inefficient designs and extra material usage which can add to the cost of the products.

Other systems such as buttons, snaps, hooks and eyes, and ties are limited in that they connect discrete points only. If only one fastening device is used for a particular closure, the connection allows material around the fastener to rotate around the discrete points connected by the fastener. Further, if a span other than a single point needs to be connected, these systems generally require more than one fastening device per closure. Multiple connections can be cumbersome and can result in gapping between the discrete fastening device components, particularly if the connection is under stress. These systems also require precise alignment of the components to create the connection desired. Some point to point fastening systems require that forces be maintained on the system throughout the time the fastener is connected.

Other examples of interlocking closures can be found in U.S. Pat. No. 198,097 issued to Fries on Dec. 11, 1877, U.S. Pat. No. 207,253 issued to Chipley on Aug. 20, 1878, U.S. Pat. No. 378,874 issued to Davis on Mar. 6, 1888, U.S. Pat. No. 771,719 issued to Copeland on Oct. 4, 1904, U.S. Pat. No. 791,654 issued to Searle on Jun. 6, 1905, U.S. Pat. No. 2,837,096 issued to Leveillee on Jun. 3, 1958, U.S. Pat. No. 3,482,289 issued to Stradella on Dec. 9, 1969, U.S. Pat. No. 3,620,180 issued to Waldes on Nov. 16, 1971, U.S. Pat. No. 3,834,824 issued to Jahn on Sep. 10, 1974, and U.S. Pat. No. 4,001,924 issued to Bengtsson on Jan. 11, 1977. All of these fasteners can join lengths or spans, but each suffers from at least one important disadvantage, especially for use with disposable products like diapers. Some require the user to press on the connection to create engagement. Others require intricate manipulation to engage, such as tucking a tab over one element then below another. Yet others require at least one element to deform to create engagement which may limit the load bearing capability of the fastener. Most lack provisions for allowing the fastener to conform to different shaped surfaces while in use and many of the systems have no provisions allowing for adjustable fit. Further, if used in disposable absorbent products such as diapers, these fasteners can cause skin marking and discomfort for the wearer.

Thus, it would be advantageous to provide an improved fastening device. Further, it would be advantageous to provide a refastenable fastening device which allows easy connection of lengths or spans, rather than discrete points. It would also be advantageous to provide a refastenable fastening device which allows adjustability and which is suitable for many uses, including disposable products, absorbent articles, and especially disposable absorbent articles. To this end, it would be desirable to provide a fastening device which readily conforms to different shapes when in use and/or which minimizes skin marking when used on a product to be worn close to the skin. Further, it would be advantageous to provide an absorbent article having a fastening device which can easily be engaged in many different configurations, such as when the wearer is sitting, lying down or standing. Accordingly, it is an object of the present invention to provide disposable products which include improved tab and slot fastening devices.

SUMMARY OF THE INVENTION

The present invention is directed to an improved fastening device suitable for use with disposable absorbent articles. The fastening device preferably includes a tab member and a slot member. The slot member has an inboard portion, an outboard portion and a slot which may include a slit or a loop. The inboard portion located laterally inboard of the outboard portion and the slot located between the inboard portion and the outboard portion. The tab member has a length, a proximal edge, a distal edge and a lip portion. The tab portion is passed through the slot of the slot member to engage the fastening device. Once passed through the slot, at least the lip portion of the tab member overlaps the outboard portion of the slot member to prevent the tab member from disengaging from the slot member. The present invention is also directed to articles which include the tab and slot fastening device. Some article with which the fastening device is known to be useful include diapers, catamenial pads, bibs, wraps, packages and the like. However, the invention is not limited to such uses, but rather is directed to all other suitable uses of the tab and slot fastening device.

The fastening device of the present invention may provide a solution for any or all of the deficiencies identified with respect to other known fasteners. For example, the tab and slot fastening device of the present invention is strong and simple to use, yet it can be configured to conform to shaped surfaces and to be otherwise skin-friendly. The tab and slot fastening device can be adjusted and refastened without damage to the article or to the fastener. Further, the tab and slot fastening device can evenly join lengths or spans of material without the need for multiple fasteners. And, because the tab and slot fastener has a designated fastening configuration, no extra material is needed to ensure proper fastening of the fastener as in tapes and hook and loop fasteners. Further, especially important for disposable products, such as diapers, is the fact that the tab and slot fastener can form a connection between panels without the need for overlapping the panels. This allows for a reduction in the amount of material in the disposable article, and thus, reduces the overall cost of the article. Accordingly, the tab and slot fastening device of the present invention can be provided with the benefits of conventional fastening systems without many of the disadvantages.

BRIEF DESCRIPTION OF THE DRAWINGS

While the specification concludes with claims particularly pointing out and distinctly claiming the subject matter which is regarded as forming the present invention, it is believed that the invention will be better understood from the following description which is taken in conjunction with the accompanying drawings in which like designations are used to designate substantially identical elements, and in which:

FIG. 20A is a top-down view, i.e., a head-to-toe view, of a body bisected at the waist.

FIG. 20B is a side view of a baby in the "neutral" position of the hip joint in which the baby's back and legs are generally in a vertical orientation.

FIG. 20C is a side view of a baby in a bent position of the hip joint in which the baby's legs are generally in a horizontal orientation.

FIG. 22A is a plan view of a portion of a fastening device of the present invention.

FIG. 22B is a side view of a portion of a fastening device of the present invention.

FIG. 22C is a side view of a fastening device of the present invention.

FIG. 22D is a plan view of a portion of a fastening device of the present invention.

DETAILED DESCRIPTION OF THE INVENTION

As used herein, the term "absorbent article" refers to devices which absorb and contain body exudates, and, more specifically, refers to devices which are placed against or in proximity to the body of the wearer to absorb and contain the various exudates discharged from the body. The term "disposable" is used herein to describe absorbent articles which are not intended to be laundered or otherwise restored or reused as an absorbent article (i.e., they are intended to be discarded after a single use and, preferably, to be recycled, composted or otherwise disposed of in an environmentally compatible manner). A "unitary" absorbent article refers to an absorbent article which is formed of separate parts united together to form a coordinated entity so that it does not require separate manipulative parts like a separate holder and liner. As used herein, the term "diaper" refers to an absorbent article generally worn by infants and incontinent persons that is worn about the lower torso of the wearer. It should be understood, however, that the present invention is also applicable to other absorbent articles such as incontinent briefs, incontinent undergarments, diaper holders and liners, feminine hygiene garments, medical wraps, bibs, bandages, and the like. A preferred embodiment of an absorbent article of the present invention is the unitary disposable absorbent article, diaper 20, shown in FIG. 1.

Figure 1:
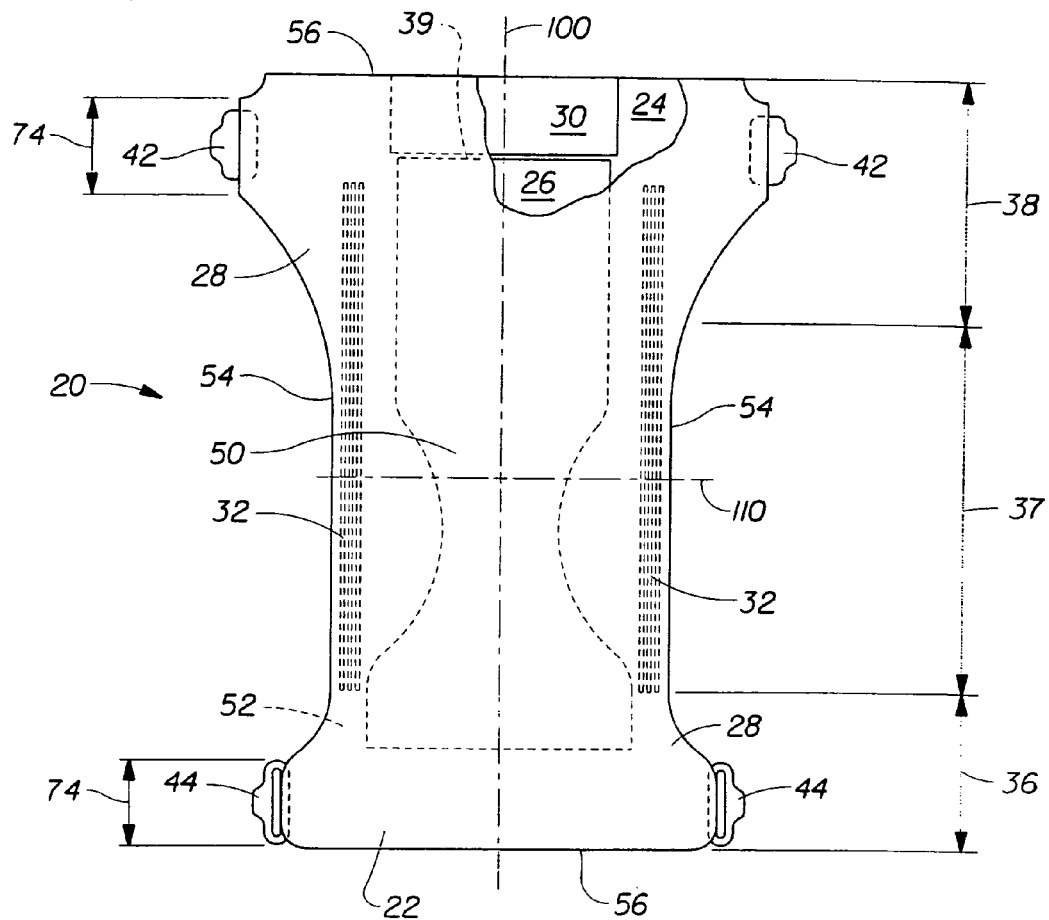
FIG. 1 is a plan view of an absorbent article in its flat out uncontracted state with the body-facing surface facing the viewer.

FIG. 1 is a plan view of one preferred embodiment of a diaper 20 including the fastening device 41 of the present invention in its flat-out, uncontracted state (i.e., with elastic induced contraction pulled out) with portions of the structure being cut-away to more clearly show the construction of the diaper 20. The portion of the diaper 20 which faces or contacts the wearer, the inner surface 50, is oriented towards the viewer. As shown in FIG. 1, the diaper 20 preferably comprises a liquid pervious topsheet 22; a liquid impervious backsheet 24 joined with the topsheet 22; an absorbent core 26 positioned between the topsheet 22 and the backsheet 24; side panels 28; leg cuffs 32; and a waist feature 30. (As used herein, the term "joined" encompasses configurations whereby an element is directly secured to the other element by affixing the element directly to the other element, and configurations whereby the element is indirectly secured to the other element by affixing the element to intermediate member(s) which in turn are affixed to the other element.)

The diaper 20 is shown in FIG. 1 to have an outer surface 52, an inner surface 50 opposed to the outer surface 52, first waist region 36, a second waist region 38 opposed to the first waist region 36, a crotch region 37 positioned between the first waist region 36 and the second waist region 38. The diaper 20 also has longitudinal edges 54 and end edges 56. The inner surface 50 of the diaper 20 generally comprises that portion of the diaper 20 which is positioned adjacent to the wearer's body during use (i.e., the inner surface 50 generally is formed by at least a portion of the topsheet 22 and other components joined to the topsheet 22). The outer surface 52 generally comprises that portion of the diaper 20 which is positioned away from the wearer's body (i.e., the outer surface 52 generally is formed by at least a portion of the backsheet 24 and other components joined to the backsheet 24). The diaper 20 also has a longitudinal centerline 100 and a lateral centerline 110.

FIG. 1 shows a preferred embodiment of the diaper 20 in which the topsheet 22 and the backsheet 24 have length and width dimensions generally larger than those of the absorbent core 26. The topsheet 22 and the backsheet 24 extend beyond the edges of the absorbent core 26 to thereby form the periphery of the diaper 20. While the topsheet 22, the backsheet 24, and the absorbent core 26 may include many different materials and may be assembled in a variety of well known configurations, preferred diaper materials and configurations are described generally in U.S. Pat. No. 3,860,003 entitled "Contractable Side Portions for Disposable Diaper" which issued to Kenneth B. Buell on Jan. 14, 1975; and U.S. Pat. No. 5,151,092 issued to Buell on Sep. 9, 1992; and U.S. Pat. No. 5,221,274 issued to Buell on Jun. 22, 1993; each of which is incorporated herein by reference.

The absorbent core 26 may be any absorbent means which is generally compressible, conformable, non-irritating to the wearer's skin, and capable of absorbing and retaining liquids such as urine and other certain body exudates. The absorbent core 26 may be manufactured in a wide variety of sizes and shapes (e.g., rectangular, hourglass, "T"-shaped, asymmetric, etc.) and from a wide variety of liquid-absorbent materials commonly used in disposable diapers and other absorbent articles such as comminuted wood pulp which is generally referred to as airfelt. Examples of other suitable absorbent material include creped cellulose wadding; meltblown polymers including coform; chemically stiffened, modified or cross-linked cellulosic fibers; tissue including tissue wraps and tissue laminates; absorbent foams; absorbent sponges; superabsorbent polymers; absorbent gelling materials; or any equivalent material or combinations of materials.

The backsheet 24 is preferably impervious to liquids (e.g., urine) and is preferably manufactured from a thin plastic film or a nonwoven web, although other flexible liquid impervious materials may also be used. As used herein, the term "flexible" refers to materials which are compliant and will readily conform to the general shape and contours of the human body. The backsheet 24 prevents the exudates absorbed and contained in the absorbent core 26 from wetting articles which contact the diaper 20 such as bedsheets and undergarments. The backsheet 24 may thus comprise a woven or nonwoven material, polymeric films such as thermoplastic films of polyethylene or polypropylene, or composite materials such as a film-coated nonwoven material. Preferably, the backsheet is a thermoplastic film having a thickness of from about 0.012 mm (0.5 mil) to about 0.051 mm (2.0 mils). Some preferred materials for the backsheet include X15306 film, X10964 film and X 10962 film manufactured by Tredegar Industries, Inc. of Terre Haute, Ind. The backsheet 24 is preferably embossed and/or matte finished to provide a more clothlike appearance. Further, the backsheet 24 may permit vapors to escape from the absorbent core 26 (i.e., breathable) while still preventing exudates from passing through the backsheet 24. In one embodiment, the backsheet 26 may comprise a structural elastic-like film (SELF) web. SELF webs suitable for the present invention are more completely described in the commonly assigned U.S. Pat. No. 5,518,801 entitled "Web Materials Exhibiting Elastic-Like Behavior" issued to Chappell et al. on May 21, 1996, which is incorporated herein by reference.

The topsheet 22 is preferably compliant, soft feeling, and non-irritating to the wearer's skin. Further, the topsheet 22 is preferably liquid pervious, permitting liquids (e.g., urine) to readily penetrate through its thickness. A suitable topsheet may be manufactured from a wide range of materials, such as porous foams; reticulated foams; apertured plastic films; or woven or nonwoven webs of natural fibers (e.g., wood or cotton fibers), synthetic fibers (e.g., polyester or polypropylene fibers), or a combination of natural and synthetic fibers. Preferably, the topsheet 22 is made of a hydrophobic material to isolate the wearer's skin from liquids contained in the absorbent core 26. There are a number of manufacturing techniques which may be used to manufacture the topsheet 22. For example, the topsheet 22 may be a nonwoven web of fibers spunbond, carded, wet-laid, meltblown, hydroentangled, combinations of the above, or the like. One preferred topsheet is carded and thermally bonded by means well known to those skilled in the fabrics art. The topsheet may comprise a web of staple length polypropylene fibers such as P-8 manufactured by Veratec, Inc., a Division of International Paper Company, of Walpole, Mass. Another preferred topsheet includes formed films as described in U.S. Pat. No. 3,929,135, issued to Thompson on Dec. 30, 1975; U.S. Pat. No. 4,324,246 issued to Mullane et al. on Apr. 13, 1982; U.S. Pat. No. 4,342,3145 issued to Radel et al on Aug. 3, 1982; U.S. Pat. No. 4,463,045 issued to Ahr et al. on Jul. 31, 1984; and U.S. Pat. No. 5,006,394 issued to Baird on Apr. 9, 1991. Each of these patents are hereby incorporated by reference herein.

The diaper 20 preferably further comprises leg cuffs 32 to improve containment of liquids and other body exudates. Each elasticized leg cuff may include several different embodiments for reducing the leakage of body exudates in the leg regions. (The leg cuff can also be referred to as leg bands, side flaps, barrier cuffs, or elastic cuffs.) U.S. Pat. No. 3,860,003 describes a disposable diaper which provides a contractible leg opening having a side flap and one or more elastic members to provide an elasticized leg cuff (gasketing cuff). U.S. Pat. No. 4,909,803 entitled "Disposable Absorbent Article Having Elasticized Flaps" issued to Aziz et al. on Mar. 20, 1990, describes a disposable diaper having "stand-up" elasticized flaps (barrier cuffs) to improve the containment of the leg regions. U.S. Pat. No. 4,695,278 entitled "Absorbent Article Having Dual Cuffs" issued to Lawson on Sep. 22, 1987, describes a disposable diaper having dual cuffs including a gasketing cuff 31 and a barrier cuff 32.

The diaper 20 preferably also includes a waist feature 30 that helps provide improved fit and containment. The waist feature 30 is that portion or zone of the diaper 20 which is intended to elastically expand and contract to dynamically fit the wearer's waist. The elastic waist feature 30 generally extends longitudinally outwardly from at least one of the waist edges 39 of the absorbent core 26 and generally forms at least a portion of the end edge 56 of the diaper 20. Although disposable diapers are generally constructed so as to have two elastic waist features, one positioned in the first waist region 36 and one positioned in the second waist region 38, diapers can be constructed with a single elastic waist feature 30. Further, while the elastic waist feature 30 or any of its constituent elements can include a separate element affixed to the diaper 20, the elastic waist feature 30 is preferably constructed as an extension of other elements of the diaper 20 such as the backsheet 24, the topsheet 22 or both the backsheet 24 and the topsheet 22. Examples of suitable waist features include those described in U.S. Pat. No. 4,515,595 issued to Kievit et al. on May 7, 1985 and the above referenced U.S. Pat. No. 5,151,092 issued to Buell on Sep. 9, 1992; and U.S. Pat. No. 5,221,274 issued to Buell on Jun. 22, 1993; each of which is incorporated herein by reference.

The diaper 20 preferably also includes a fastening system 40 which joins at least a portion of the first waist region 36 of the diaper 20 with at least a portion of the second waist region 38, preferably to form leg and waist openings. The fastening system 40 also works with the waist feature(s) 30 to maintain lateral tension in order to keep the diaper 20 in place about the wearer. As shown in FIG. 1, the fastening system 40 may be the primary fastening system for joining the first and second waist regions 36 and 38. (As used herein, "primary fastening system" refers to a fastening system which is used to hold the diaper in its constructed, in use configuration about the wearer. Thus, the primary fastening system generally must be strong enough to remain fastened throughout the article's normal time of use when subjected to the dynamic forces created by the wearer's movements.) However, the fastening system 40 may be used alone or in conjunction with other fastening means such as hook and loop fasteners, tape fasteners, snaps, buttons and the like to provide different fastening characteristics. For example, the fastening system 40 may provide the diaper 20 with a disposal means for fastening the diaper 20 in a configuration convenient for disposal. Further, secondary fastening means may provide the diaper 20 with a means for adjusting fit or may increase the strength of the connection between the first waist region 36 and the second waist region 38. (As used herein, "secondary fastening means" refers to fastening means which are not intended to independently hold the diaper 20 in its constructed configuration about the wearer, but rather to complement the primary fastening system by providing additional benefits generally related to fit, adjustability, disposability and the like.)

Figure 4:
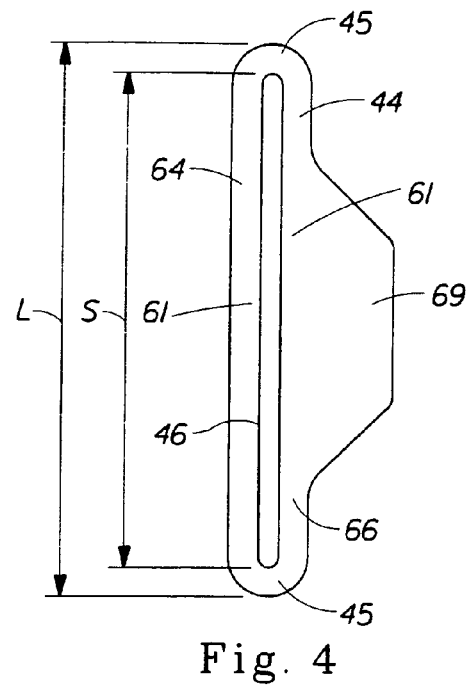
FIG. 4 is a plan view of a portion of the fastening device of the present invention.
Figure 13:
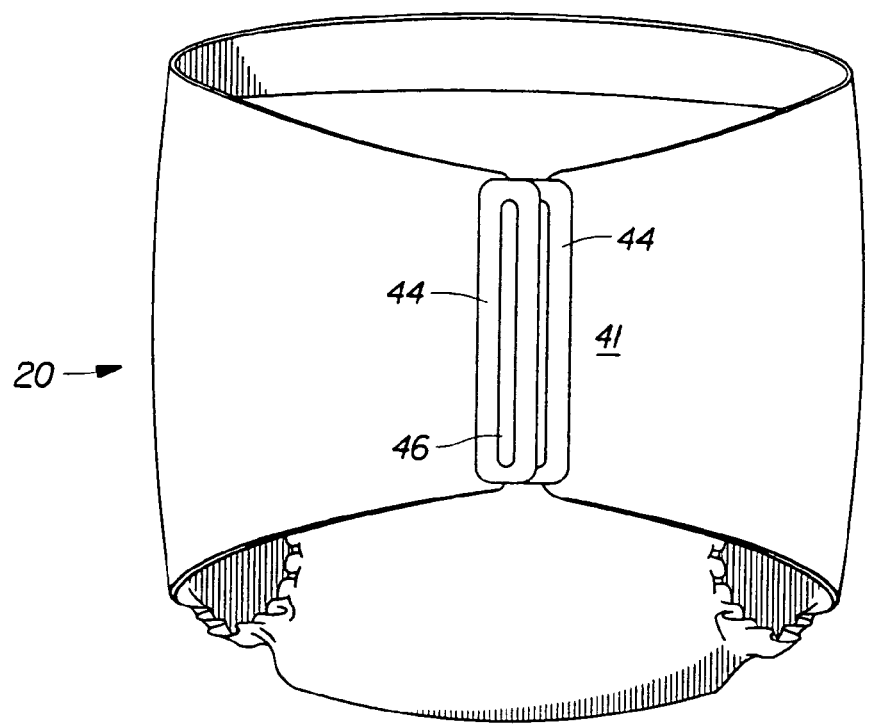
FIG. 13 is a perspective view of an alternative embodiment of the present invention in a fastened configuration.
Figure 19:
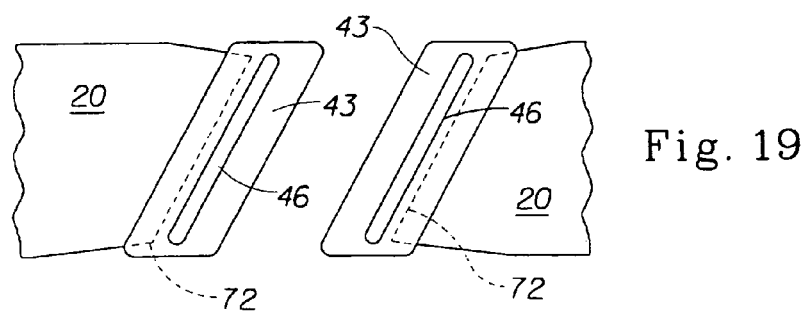
FIG. 19 is a plan view of one embodiment of the fastening device of the present invention in an unfastened configuration.

The fastening system 40 preferably includes fastening device 41 which comprises a tab member 42 and a slot member 44. (Embodiments are contemplated, however, wherein the fastening device 41 includes at least two slot members 44 which can be engaged with each other as shown in FIG. 13. Alternative embodiments may include combined tab/slot members 43, as shown in FIG. 19.) The tab member 42 preferably includes a generally elongate member having a proximal edge 60, a distal edge 62, a lip portion 48 and a length T. The slot member 44 includes an inboard portion 64, an outboard portion 66 and a slot 46 disposed between the inboard portion 64 and the outboard portion 66. The slot member 44 has a length L and the slot 46 has a length S, as shown in FIG. 4.

Figure 7:
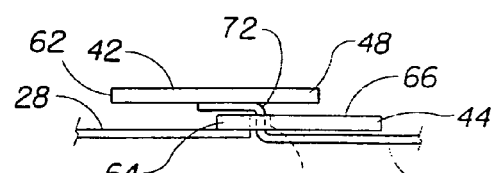
FIG. 7 is an end view of the embodiment of the fastening device shown in FIG. 6.

In a simple form, the fastening device 41 is fastened by passing the tab member 42 completely through the slot 46 of the slot member 44. (In embodiments including two or more slot members 44 which engage one another, one of the slot members 44 will be passed through the other slot member 44 to fasten the device 41, as shown in FIG. 13.) Once the tab member 42 has been passed through the slot member 44, as shown in FIGS. 7, the lip portion 48 of the tab member 42 is rotated into a plane generally parallel with the plane of the slot member 44 such that at least a part of the lip portion 48 is overlapping at least a part of the outboard portion 66 of the slot member 44. In this configuration, the lip portion 48 of the tab member 42 will prevent the tab member 42 from slipping back through the slot 46 and disengaging the fastening device 41. A portion of the tab member 42 or the material of the article to which the tab member 42 is joined will extend into the slot 46, as shown in FIG. 7. The material in the slot 46 will act to resist forces in shear which tend to direct the tab member 42 and the slot member 44 apart.

The Tab Member

Figure 5:
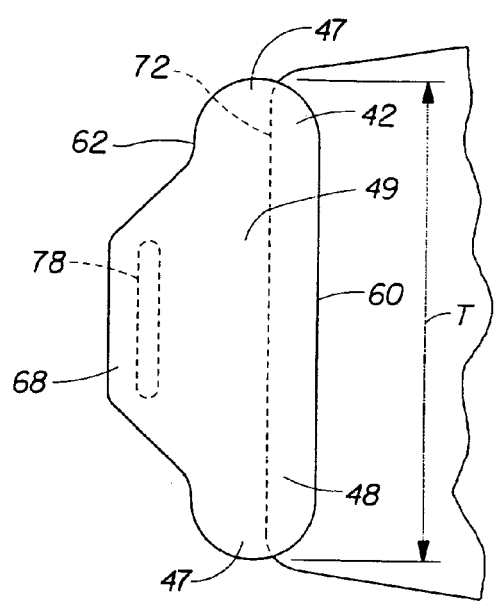
FIG. 5 is a plan view of a portion of the fastening device of the present invention.

As shown in FIG. 5, the tab member 42 is preferably an elongated member having a length T, a proximal edge 60, a distal edge 62, and a lip portion 48 generally adjacent at least a portion of the proximal edge 60. The tab member preferably has longitudinal ends 47 and a central region 49. The lip portion 48 is that portion of the tab member 42 which is not joined directly to the underlying structure of the article to which the tab member 42 is attached. As noted above, the lip portion 48 should lift away from the underlying structure of the article so that it can be positioned in an overlapping configuration with at least a portion of the outboard portion 66 of the slot member 44 when in use. Some preferred embodiments of the tab member 42 may also include a grip portion 68 generally adjacent to and extending outwardly from the distal edge 62 of the tab member 42. The grip portion 68 helps the user grip the tab member 42 when fastening or releasing the fastening device 41 and preferably extends from the distal edge 62 in the central region 49 of the tab member 42.

The tab member 42 may be of any size and/or shape and may be made from any suitable material. Generally, however, the tab member 42 should be sized to fit through the slot 46 of the slot member 44 with little or no bending or deformation of either component. The shape of the tab member 42 will often be dependent on the end use of the fastening device 41, but in any case should be aesthetically pleasing, easy to hold and maneuver, and capable of maintaining the device 41 in a fastened configuration throughout the intended period of use when subjected to expected forces and external conditions. The tab member 42 may be designed so that the member or a portion or portions of the tab member 42 are located outside of a "compressive" region of a wearer. A compressive region of the wearer is a region in which the natural bodily movement of the wearer will move towards the region. An "expanding" region of a wearer, however, is a region in which the natural body movement of the wearer will move away from the region. There are several compressive and expanding regions on the body of a wearer, especially where there are joints that bend such as knees, elbows, shoulders, hips, ankles, wrists, etc. In order to determine whether a particular region of the body is a compressive or expanding zone within the scope of the present invention, the change in the surrounding anatomical structure of the region is examined as a joint is moved from a "neutral" position to a bent position. A neutral position is defined as the position when the joint is not bent, i.e., the position with the muscles generally relaxed and not attempting to flex the joint. If the surrounding anatomical structure, e.g., tissues, bones, etc., would tend to compress or bend an object on the body's surface as the joint is moved from a neutral to a flexed position, the region is defined as a compressive region. If the surrounding anatomical structure would tend to expand or stretch an object on the body's surface, the region is defined as an expanding region. FIG. 20A, for example, shows a top down view, i.e., a head-to-toe view, of a body bisected at the waist. In this example, the regions shown are particularly applicable to regions of interest for the application of a diaper. The back region, B, denotes a region across the back of the wearer, which may include a portion of the tissues and muscle associated with the leg; the side regions, S1 and S2, denote side regions of the wearer; and front region, F, denotes the front or pubic region of the wearer. FIG. 20B shows a side view of a baby in the "neutral" position for the hip joint in which the baby's back and legs are generally in a vertical orientation. FIG. 20C shows a side view of the baby in a bent position in which the baby's legs have been raised to a generally horizontal orientation. The FIGS. 20B and 20C are connected by dotted axes that show the relative location of two points on the body surface in the side and back regions in neutral and bent positions, respectively. The side regions S1 and S2, for example, are compressive because the vertical distance between two points on the skin surface in the region becomes smaller as the wearer's leg lifts or the wearer bends at the waist. In the back region B, behind the legs of the wearer, however, the vertical distance between two points on the skin of the wearer tends to increase in all but extreme rearward leg motions. With respect to a diaper for application on babies, motions such as sitting and leaning forward are more prevalent, and, thus, the back region B is typically considered an expanding region because these motions result in the vertical distance between two points on the skin of the wearer increasing. In extreme rearward leg motions such as when the leg moves substantially backward and the back is held vertical, the vertical distance between two points on the skin of the wearer may decrease. This, however, is much less likely to occur than the legs being brought forward or the wearer leaning forward. For example, when the wearer runs, the leg is brought substantially backward, but the wearer also tends to lean forward and the vertical distance between two points on the skin of the wearer in the region may not be brought closer together. The principle of avoiding compressive regions and utilizing expanding regions may also be applied to the design of tab members for articles other than diapers such as, but not limited to, sanitary napkins, bibs and wraps placed on other parts of the wearer.

Figure 21:
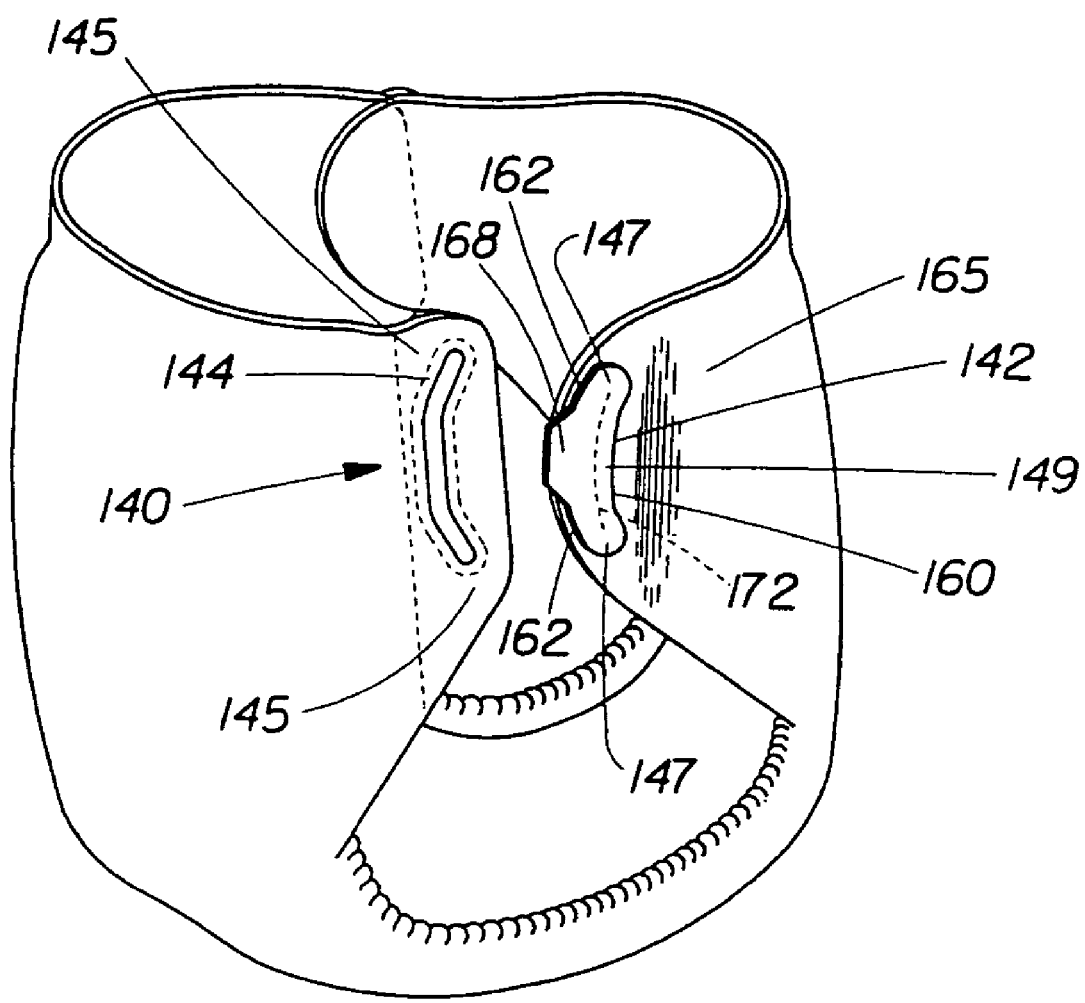
FIG. 21 is a perspective view of an absorbent article embodiment of the present invention.

In a preferred embodiment of the present invention, the tab member 42 or a portion of that tab member 42, when fastened, may be located in an expanding region of a wearer so that, as the wearer moves, longitudinal compressive forces from the body applied to the tab member 42 will be minimized. In a waist fastening system 140 for a diaper 120 shown in FIG. 21, for example, the tab member 142 has a nonlinear distal edge 162 compared to the distal edge 62 shown in FIG. 5, which is generally linear with the exception of the grip portion 68 extending from the central region 49 of the tab member 42 and the rounding of the longitudinal ends for aesthetic and comfort reasons. The "C-shaped" distal edge 162 of this embodiment allows the central region 149 of the tab member 142 to be located forward towards the front of the wearer and the longitudinal ends 147 of the tab member 142 to be located farther back and away from a compressive region of the wearer. This allows the caretaker to more easily grab the grip portion 168 that preferably extends forward from the central region 149 of the tab member 142 when affixing the diaper to the wearer, but also allows the longitudinal ends 147 to be swept back away from the compressive region where the wearer's leg flexes toward the torso. This reduces the chance that the wearer's skin will be pressed up against the tab member 142 and, therefore, reduces the chance of skin marking or irritation. Alternatively, portions of the tab member 142 such as, but not limited to, the distal edge 162, one or more of the longitudinal ends 147, the proximal edge 160 of the tab member 142 or the line of attachment 172 between the tab member 142 and the retaining material 165 may include other linear or non-linear shapes including a "D-shape," a "U-shape," a "V-shape" or any other design in order to minimize the possibility of skin marking or skin irritation of the wearer. For example, the shape of the tab member 142 may allow a portion of the tab member 142 to be removed from a compressive region of the wearer or minimize the portion of the tab member 142 in a compressive region. Further, it may be desirable to locate different portions of the tab member 42 in different orientations to avoid compressive regions. For example, only one of the longitudinal ends 47 of the tab member may be swept backward or forward of the central region 49, or each of the longitudinal ends 47 may be oriented in opposite directions away from the central region 49 such as the top longitudinal end being swept forward and the bottom longitudinal end being swept rearward or vice versa.

The materials which make up the tab member 42 should also be chosen depending on the end use of the fastening device 41. For example, if the fastening device 41 is to be used in a diaper, as shown in FIG. 1, the tab member 42 may include any material suitable for such a use, including but not limited to plastics, films, foams, nonwoven webs, woven webs, paper, laminates, steel, fiber reinforced plastics and the like, or combinations thereof. In embodiments where the fastening device is used near or against the skin of a human or animal, it is preferred that the materials making up the tab member 42 be flexible. The flexibility allows the fastening device 41 to conform to the shape of the body and thus, reduces the likelihood that the fastening device 41 will irritate or injure the wearer's skin.

Figure 2:
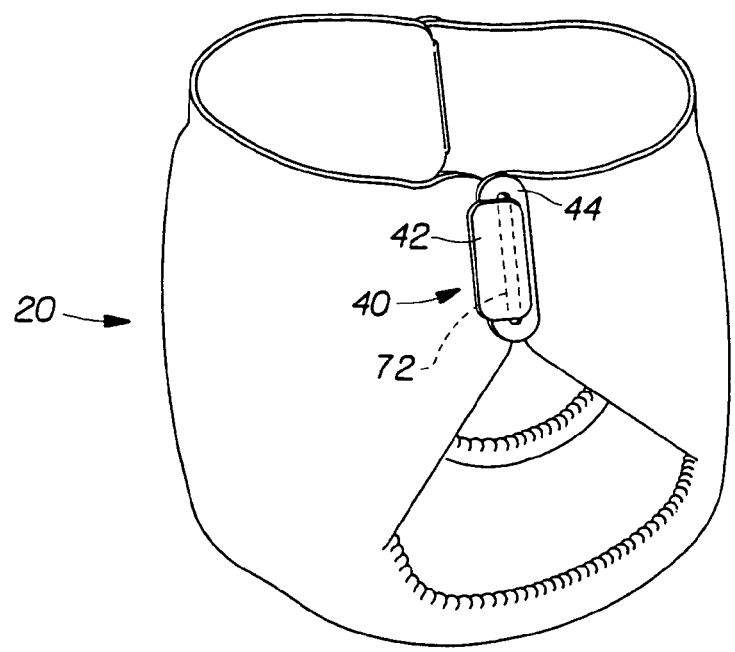
FIG. 2 is a perspective view of an absorbent article embodiment of the present invention.
Figure 3:
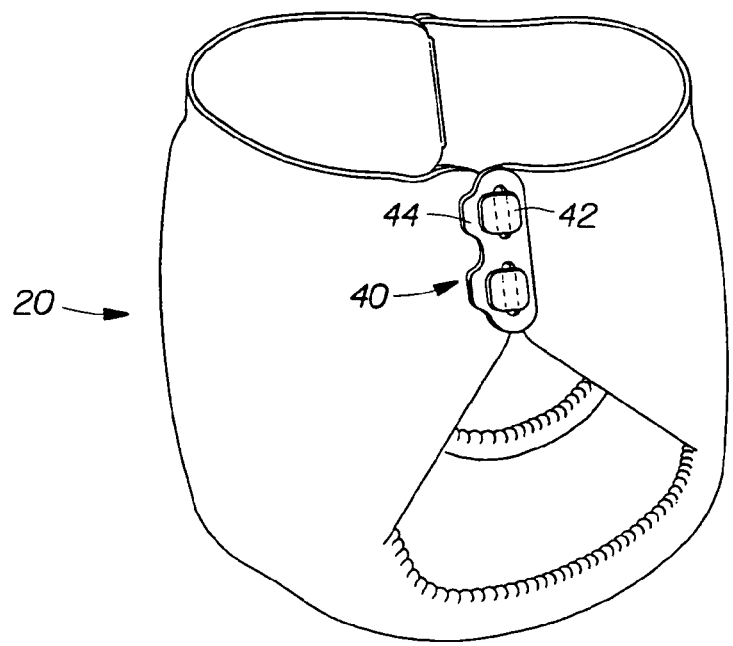
FIG. 3 is a perspective view of an alternative absorbent article embodiment of the present invention.
Figure 6:
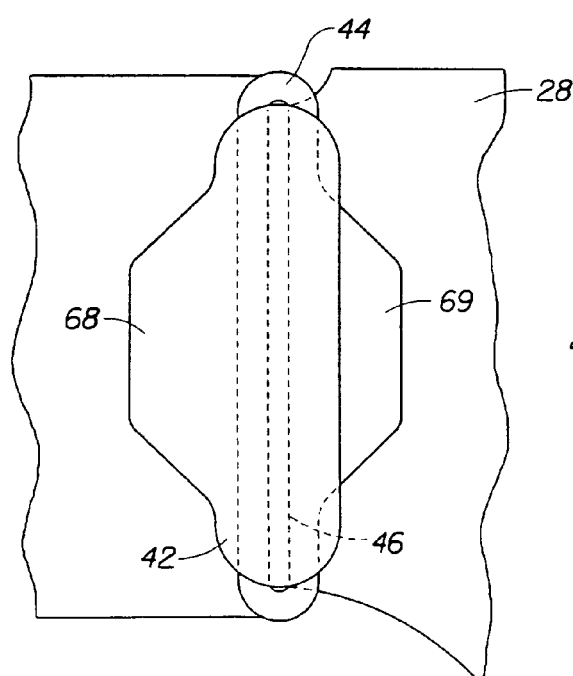
FIG. 6 is a plan view of one embodiment of the fastening device of the present invention in a fastened configuration.
Figure 9:
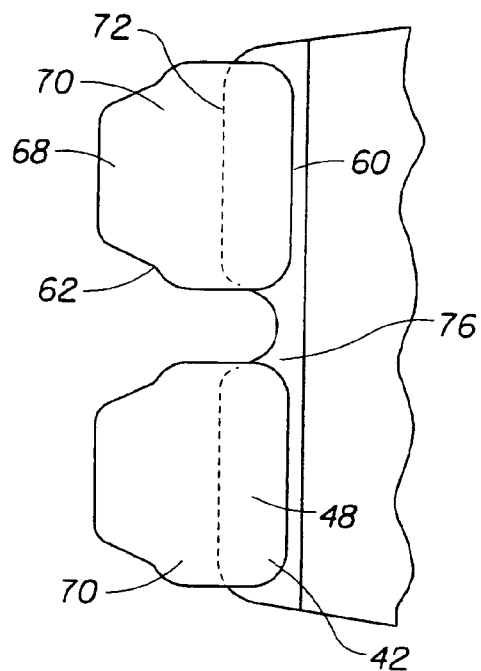
FIG. 9 is a plan view of a portion of the fastening device of the present invention.
Figure 10:
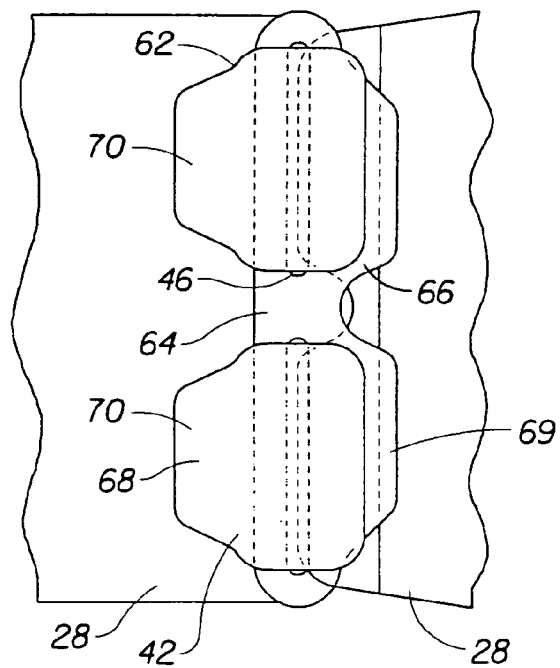
FIG. 10 is a plan view of one embodiment of the fastening device of the present invention in a fastened configuration.

The tab member 42 may include one or more tab elements 70. A tab member 42 with a single tab element 70 is shown in FIGS. 1, 2 and 6. A tab member 42 with more than one tab element 70 is shown in FIGS. 3, 9 and 10. If the tab member 42 includes more than one tab element 70, the tab elements are preferably operatively associated with each other. (As used herein, the term "operatively associated" refers to elements which are directly or indirectly joined together so as to function generally as a single element. The term "directly joined" refers to elements which are joined to each other without any intermediate elements joined therebetween, except for the means joining the elements (i.e. the adhesive). The term "indirectly joined" refers to elements joined with each other by means of an element or elements other than the joining means.) Thus, the tab member 42, regardless of the number of tab elements 70, functions as a single element of the fastening device 41. This is important to reduce the complexity of the fastening device 41 and to ensure that a single fastening motion can engage the entire tab member 42, whether the tab member 42 includes one or more tab elements 70.

The tab member 42 may be unitary with the article to which it is attached or may be a separate element joined thereto. The tab member 42 may be joined to the article at any location. In a disposable absorbent article embodiment, such as that shown in FIG. 1, the tab member 42 may be an extension of the material making up the side panel 28. In such cases, it may be preferable to provide additional material or to process the material of the side panel 28 so as to change some of its physical properties. For example, it may be desirable that the side panel 28 be extensible and the tab member 42 not be extensible. Further, it may be desirable to ensure proper fastening that the tab member 42 be stronger and/or stiffer than the side panel 28. Alternatively, the tab member 42 may be a separate element which is joined to the article. In such cases, the tab member 42 may be made of the same or different materials than the article to which it is attached, making it easy to match the exact properties of the fastening device 41 to the intended use. Further, the material from which the tab member 42 is made can be reinforced and/or weakened at certain locations to help provide the desired flexibility and stiffness to the fastening device 41. In one embodiment the tab member 42 may be reinforced and/or weakened at one or both of its longitudinal ends 47. In other embodiments, the grip tab 69 of the tab member 42 may be reinforced and/or weakened. Methods of weakening the material include scoring, cutting, thinning, bending, heat treating, chemical treating and the like. Methods of reinforcing include heat or chemical treating the material, adding material, increasing the thickness and the like.

The tab member 42 may also include a secondary fastening member 78 which provides a different means for fastening the components of the fastening device 41 to each other, the article with which the fastening device is being used and/or other articles. For example, the tab member 42 may include secondary fastening member 78 located adjacent the distal edge 62 of the tab member 42 or adjacent the grip portion 68, as shown in FIG. 5. (Alternative embodiments are contemplated wherein the secondary fastening member 78 is located anywhere on the tab member 42.) The secondary fastening member can be used to provide the fastening device 41 with the ability to better resist shear or peel forces, greater adjustability or other properties. Further, the secondary fastening member 78 may provide the user with a means for fastening the article in a disposal configuration. The secondary fastening member 78 can be any fastening means such as hooks, loops, adhesive, cohesive, magnetic materials, static electricity, snaps and the like or any combination of these or other known fastening means.

The Slot Member

The slot member 44 is that portion of the fastening device 41 through which the tab member 42 is passed in order to engage or fasten the device. The slot member 44 has an inboard portion 64, an outboard portion 66 and a slot 46 disposed between the inboard portion 64 and the outboard portion 66. The slot member 44 preferably also includes longitudinal ends 45 and a central region 61. The slot member 44 and the slot have lengths L and S, respectively. The length S of the slot 46 is less than the length L of the slot member 42. However, the length S of the slot 46 should generally be greater than or equal to the length T of the tab member 42 such that the tab member 42 is easily passed through the slot 46 without undue bending or deformation of either component. The slot may alternatively include a slit, which is defined as a slot having essentially no gap other than that left by a cutting process. The slot member 44 may also include a grip portion 69 like that of the tab member 42. Preferably, the grip portion 69 extends laterally outwardly from the outboard portion 66 of the slot member 44. The grip portion 69 helps the user grip the slot member 44 when fastening or releasing the fastening device 41 and preferably extends from the outboard portion 66 in the central region 61 of the slot member 44.

The slot member 44 may be of any size and/or shape and may be made from any suitable material. As with the tab member 42, the shape of the slot member 44 and the materials which make up the slot member 44 will be dependent on the end use of the fastening device 41. For example, in end uses such as diapers, the slot member 44 should be designed to be skin friendly, i.e. not harmful to the wearer's skin. Thus, it may be desirable to round the edges of the fastening device 41 and to size the slot(s) 46 so as to minimize the likelihood that skin will be caught in the device 41. One way of minimizing the risk is to work the edges of the slot 46 such that they are not sharp. Another way is to make the fastening device more skin friendly include minimizing the thickness of the slot member 44 (preferably less than 0.05 inches) or to design the tab member 42 or slot member such that the slot 46 is filled in when the fastening device 41 is closed. One more way is to provide a soft or compressible material on at least the surface of the fastening device 41 which faces the wearer. Yet another way to make the fastening device more skin friendly, as described above with reference to the tab member 42, is to design the shape of the slot member 44 so that the slot member or a portion or portions of the slot member 44, when fastened, may be located in an expanding region of a wearer so that the wearer's body will not press up against the slot member 44 as the wearer moves or to minimize the portion of the slot member 44 that is located in a compressive region as described above with respect to the tab member 142. For example, see FIG. 21 in which slot member 144 is designed in a non-linear "C-shape" in order to allow the longitudinal ends 145 of the slot member 144 are swept back to remove them from the compressive region where the wearer's hip flexes forward.

As shown in FIGS. 22A, 22B and 22C, the slot member 44 may comprise a loop 244 under which the tab member 242 may be fed and interlocked. The loop 244, for example, may be a separate element connected to a portion of the article such as the backsheet of a diaper in a waist region or the crotch region of the diaper in order to provide a means of attachment to that region. Alternatively, the loop 244 may be integral with the article such as a slit in a portion of the article, e.g., a slit in the backsheet of a diaper. When the tab member 242 is interlocked with the loop 244, the retaining material 265 is affixed to the tab member at a line of attachment 272 as described above and runs under the loop 244 and holds the proximal edge 260 in contact with the loop 244. Preferably, the distance, L, from the line of attachment 272 of the retaining material 265 to the distal edge 262 of the tab member 242 is greater than the distance, H, that the loop 244 extends above the material to which it is attached, e.g., the backsheet, so that tension applied to the retaining material 265 does not pull the distal edge 262 of the tab member 242 back underneath the loop member 244. The distance H is also preferably great enough that the tab member 242 may be easily inserted under the loop 244. Further, there may be a support foundation 271 for the loop 244 to prevent the loop 244 from rolling over and allowing the tab member 244 from becoming disengaged or from deforming under load. The foundation 271 may be integral with the loop 244 or may comprise a separate element from the loop 244. If the foundation 271 is a separate element, the foundation may be directly secured to the loop 244 such as a base connected between the loop 244 and the backsheet 224 of the article such as shown in FIG. 22D. Alternatively, the foundation may be indirectly secured to the loop such as a base connected between the backsheet and the absorbent core 226 below the loop 244.

The slot member 44 may be made of materials the same as or different from the tab member 42 including plastics, films, foams, nonwoven webs, woven webs, paper, laminates, steel, fiber reinforced plastics and the like, or combinations thereof. As with the tab member 42, it may be preferred that the materials making up the slot member 44 be flexible. However, the slot member 44 should be stiff enough in the lateral direction so as not to deform and let the tab member 42 disengage under normal in use fastening forces. The material from which the slot member 44 is made can be reinforced or weakened at certain locations to help provide the desired flexibility and stiffness to the fastening device 41. In one embodiment the slot member 44 may be reinforced and/or weakened at one or both of its longitudinal ends 45. In other embodiments, the grip tab 69 of the slot member 44 may be reinforced or weakened. Methods of weakening the material include scoring, cutting, thinning, bending, heat treating, chemical treating and the like. Methods of reinforcing include heat or chemical treating the material, adding material, increasing the thickness and the like.

Figure 12:
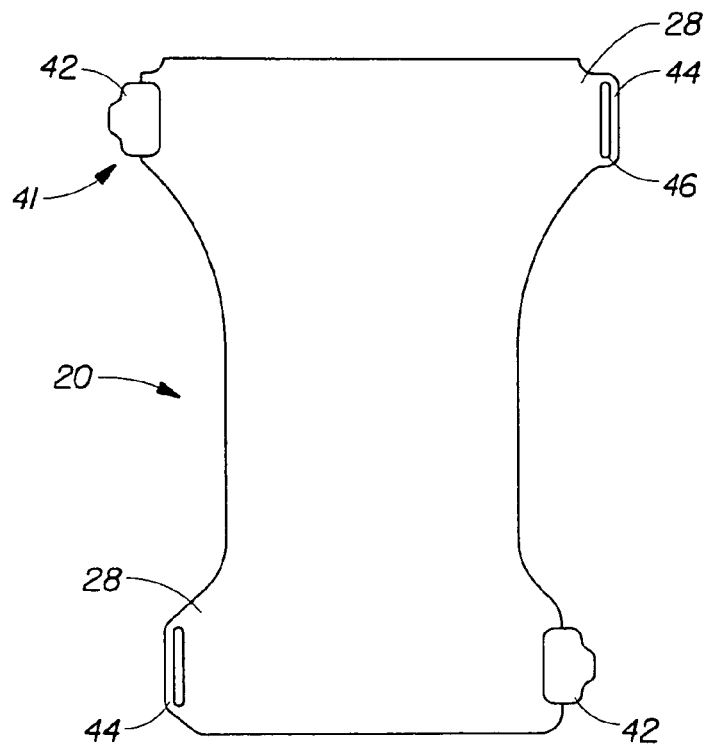
FIG. 12 is a plan view of an alternative absorbent article embodiment of the present invention in a flat out, uncontracted configuration.
Figure 14:
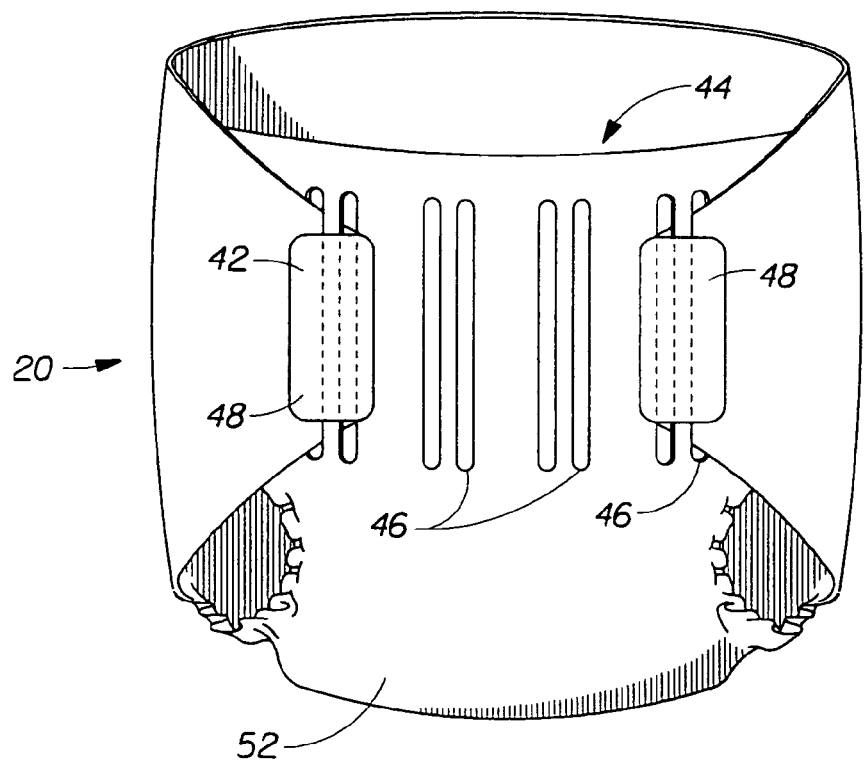
FIG. 14 is a perspective view of an alternative embodiment of the present invention in a fastened configuration.

The slot member 44 may be unitary with the article to which it is attached or may be a separate element joined thereto. Further, the slot member 44 may be joined to the article at any suitable location. In a disposable absorbent article embodiment, the slot member 44 may be an extension of the material making up the side panel 28 or any other portion of the diaper 20. As shown in FIG. 12, the slot member 44 is an extension of the side panel 28. In FIG. 14, the slot member 44 is includes the material which makes up the outer surface 52 of the diaper 20. (Embodiments are also contemplated in which the slot(s) 46 of the slot member 44 are cut through any number of layers of the article to which the fastening device 41 is attached, such as both the topsheet 24 and the backsheet 26.) Further, it may be preferable to provide additional material or to process the material of the diaper 20 so as to reinforce the slot member 44 or to change other material properties adjacent the slot 46. Alternatively, the slot member 44 may be a separate element which is joined to the article. (The slot member 44 may be joined to the article in a fixed position or may be adjustably joined to the underlying article.) In any such case, the slot member 44 may be made of the same or different materials than the article to which it is attached.

The slot member 44 may also include a secondary fastening member 78 which provides a different means for fastening the components of the fastening device 41 to each other, the article with which the fastening device is being used and/or other articles. For example, the slot member 44 may include secondary fastening member 78 located adjacent the inboard portion 64, the outboard portion 66, the grip portion 68 or any other portion of the slot member 44. As noted with regard to the tab member 42, the secondary fastening member can be used to provide the fastening device 41 with the ability to better resist shear or peel forces, greater adjustability, a disposal feature and/ or other features. The secondary fastening member 78 can be any known fastening means such those described hereinbefore and may function together with or independently of any secondary fastening member disposed on the tab member 42.

Examples of Uses for the Fastening Device

The fastening device 41 of the present invention can be used in any number of applications including fastening systems for disposable and durable absorbent articles, packages, straps, bibs, bags, belts, boxes, etc. The device is especially well suited for applications where a simple, low cost fastener will suffice, such as diapers, sanitary napkins, training pants, wraps and the like. However, modifications in the size, shape, and strength of the tab member 42 and/or slot member 44 can make the fastening device 41 suitable for more intense applications such as seat belts, straps, building materials, etc. Accordingly, the following examples of uses for the fastening device 41 should not be considered to limit the scope of the present invention.

In one preferred embodiment, as shown in FIGS. 1 and 2, the tab member 42 of the fastening device 41 is joined to one side panel 28 of the diaper 20 in the second waist region 38 and the slot member 44 is joined to the longitudinally opposing side panel 28 in the first waist region 36. (It should be noted that the embodiments are contemplated wherein the article does not include side panels which extend outwardly from the longitudinal edges 54. In such cases, the tab member 42 and/or the slot member 44 may be joined to any portion of the article in the first waist region 36, the second waist region 38 or the crotch region 37.) The tab member 42 is joined to the side panel 28 along a line of attachment 72 such that the lip portion 48 of the tab member 42 extends laterally inwardly over at least a portion of the side panel 28. The tab member 42 can be joined to any portion of the diaper 20 in any configuration. Thus, although the line of attachment 72 can be generally parallel to the longitudinal centerline 100, it can also be at any angle thereto. Alternatively, the line of attachment 72 may be non-linear such as described above with respect to the tab member 42 and the slot member 44. For example, the line of attachment may be C-shaped, D-shaped, V-shaped, etc. Angling the tab member 42 may help provide better fit of the article and more convenient fastening of the fastening device 41, as well as other benefits. The slot member 44 is shown in FIG. 1 as a separate element joined to the side panel 28, however, as noted above, the slot member 44 may be integral with any part of the diaper 20. Further, the tab member 42 may be adjustably joined to the diaper such that the position of the tab member 42 can be changed if desired.

Each side panel 28 has a longitudinal dimension 74. The longitudinal dimension 74 is the dimension of the side panel 28 measured parallel to the longitudinal centerline 100 adjacent the line of attachment 72. (In cases where the side panel extends outwardly at an angle to the lateral centerline 110, the longitudinal dimension 74 of the side panel 28 is preferably measured parallel to the line of attachment 72, and not parallel to the longitudinal centerline 100.) Preferably, the length T of the tab member 42 is greater than or equal to 25% of the longitudinal dimension 74 of the side panel 28 and more preferably greater than or equal to 50% of the longitudinal dimension 74 of the side panel 28. It is also preferred that the line of attachment 72 between the tab member 42 and the side panel 28 is greater than or equal to 25% of the length T of the tab member 42. In order to increase the stability of the tab member 42 and to distribute the forces which act on the fastening device 41 when it is fastened, it is preferred that the line of attachment 72 be greater than or equal to about 50% of the length T of the tab member 42. In especially preferred embodiments, the line of attachment 72 may be at least about 75% of the length T of the tab member 42 or the full length (about 100%) of the length T of the tab member 42. In any case, the line of attachment 72 can be continuous or intermittent so long as the forces acting on the fastener when fastened are distributed across at least about 25% of the longitudinal dimension 74 of the side panel 28 to which the tab member 42 is joined. (As used herein, the term "continuous" as it refers to the line of attachment 72 means generally uninterrupted or unbroken. The term "intermittent" as it refers to the line of attachment 72 means broken or discontinuous.)

FIGS. 3 and 10 show an alternative embodiment of the fastening device 41 of the present invention including a tab member 42 having two tab elements 70. The tab elements 70 are spaced apart longitudinally such that the tab elements 70 can attach separately through the slots 46 of the slot member 44. However, the tab elements 70 are preferably operatively associated with each other such that the fastening device 41 can be fastened and released easily. The tab elements 70 may be operatively associated by joining them to each other directly or indirectly. For example, the tab elements 70 may be joined to a stiffening member 76 which extends between the tab elements 70. The stiffening member 76 can be any material or combination of materials and can be integral with or joined to the tab member 42. In one embodiment, the stiffening member 76 includes one or more materials such as foam, film, fibers, and the like which are joined to the portion of the diaper 20 or article to which the tab member 42 is joined.

Figure 8:
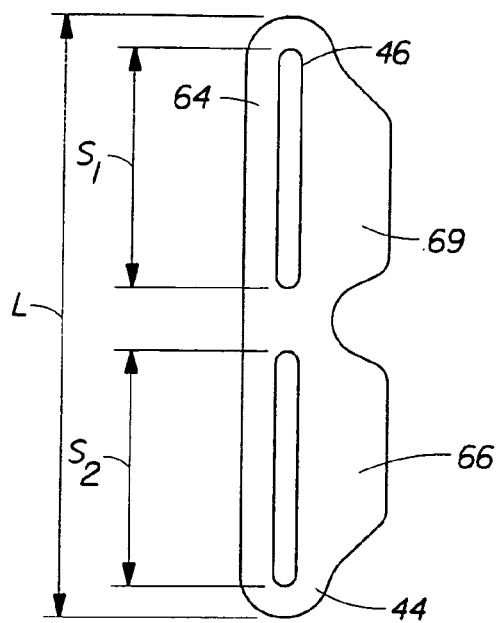
FIG. 8 is a plan view of a portion of the fastening device of the present invention.

The slot member 44 shown in FIG. 8 is suitable for use with the multi-element tab member 42 described above. The slot member 44 of FIG. 8 is shown to have two slots which are spaced apart longitudinally to correspond to the longitudinal spacing of the tab elements 70 shown in FIG. 9. The slots 46 are also shown to have length S1 and S2 which are configured such that the corresponding tab element 70 will be able to pass through without undue deformation of either member. Of course, any of the tab elements 70 can have different lengths as can the slots 46 of the slot member 44. Further, a slot member 44 suitable for use with the multi-element tab member 42 can have a single slot 46 which is sized to accommodate both tab elements 70 or may include more slots 46 than tab elements 70. Also, two or more individual slot members 44 may be provided such additional slot members 44 or additional slots 46 in the slot member 44 may provide for longitudinal adjustment of the fastening device 41.

Figure 11:
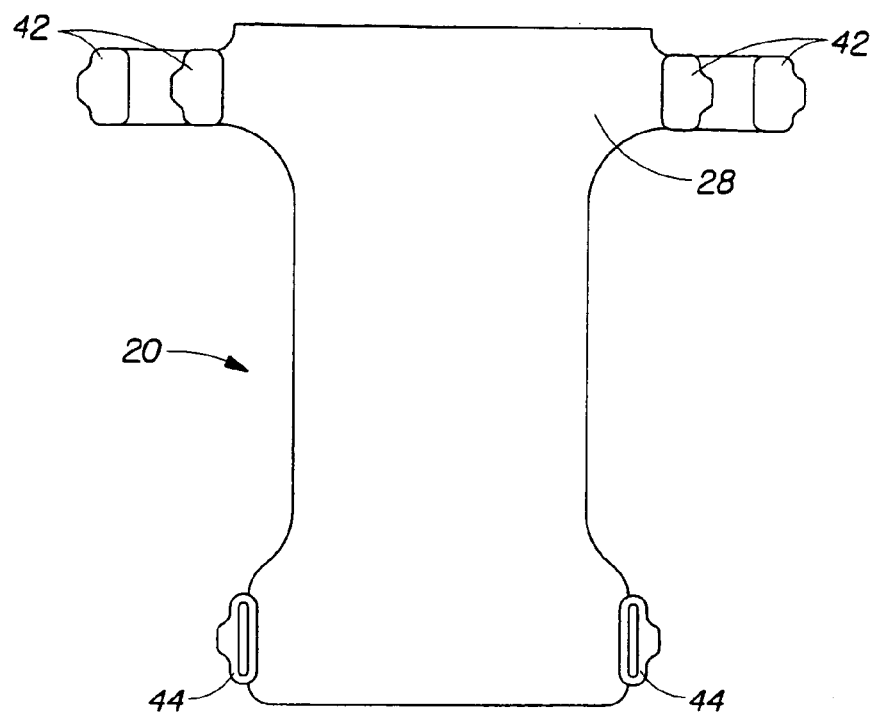
FIG. 11 is a plan view of an alternative absorbent article embodiment of the present invention in a flat out, uncontracted configuration.

As shown in FIG. 11, the article with which the fastening device 41 may be used, e.g. diaper 20, can have any number of tab members 42 capable of engaging with the slot members 44. The diaper 20 is shown to have side panels 28 including tab members 42 laterally spaced apart from each other. Such configurations are useful to provide the article with lateral adjustability such as adjustability about the waist of a diaper. In other embodiments, the diaper 20 may include multiple slot members 44 or multiple slots 46, as shown in FIG. 14. Again, this may provide the article with a means for laterally adjusting fit.

Figure 23:
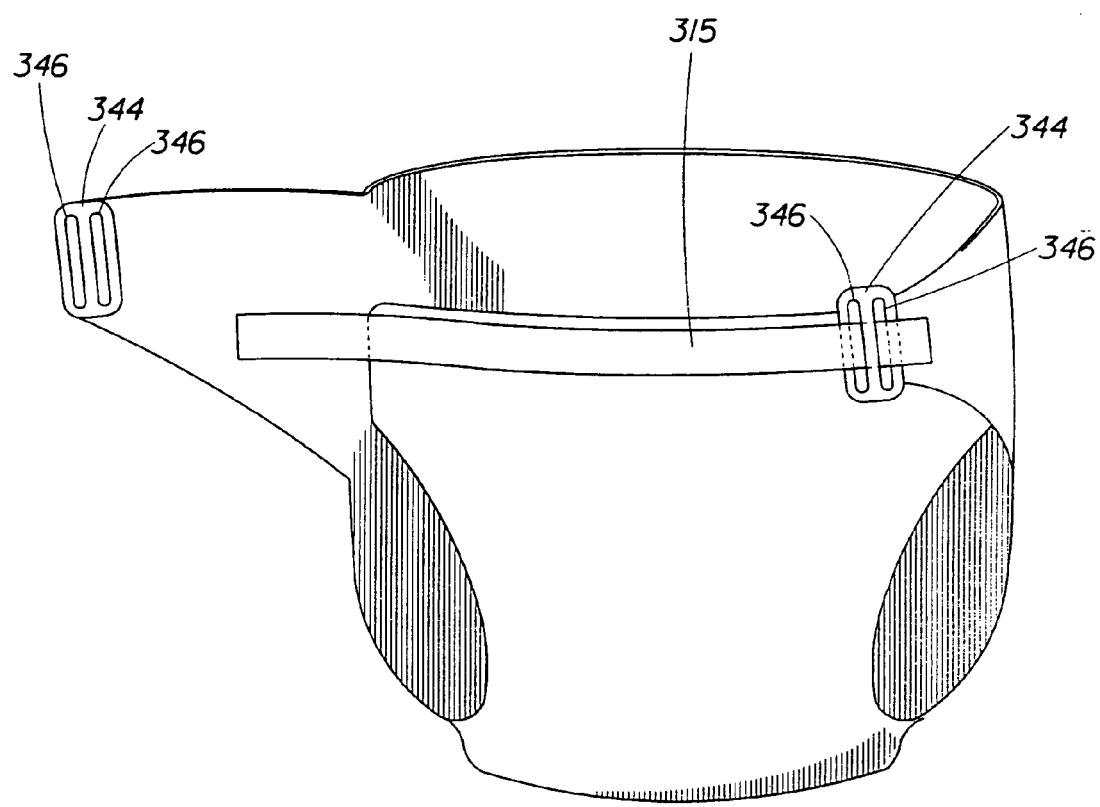
FIG. 23 is a perspective view of an absorbent article embodiment of the present invention.

In yet another embodiment the fastening device 341 may provide an adjustable fastening system in which one or more strips 315 are fed through at least one slot member 344. The strip 315 and the slot member 344 may be designed such that the friction of the strip 315 in the slot member 344 prevents the strip 315 from moving. Preferably, the friction of the strip 315 in the slot member 344 prevents the strip 315 from moving in at least the longitudinal direction. The strip 315 and the slot member 344 may also be designed so that the strip 315 may freely move in a lateral direction within the slot member 344 or lateral movement of the strip 315 within the slot member 344 may be restricted or eliminated. The lateral movement of the strip, for example, may be restricted or eliminated by friction or by placing a restraining element such as the lip portion 48 of the tab member 42 on the slot member 344. In one preferred embodiment, the fastening device 341 may include dual slot members 344, such as shown in FIG. 23, in which the strip 315 is fed through both slots 346 of the dual slot member 344 and held in place. Alternatively, two or more individual slot members 344 or an individual slot member 344 having three or more individual slots 346 may be used.

Figure 24:
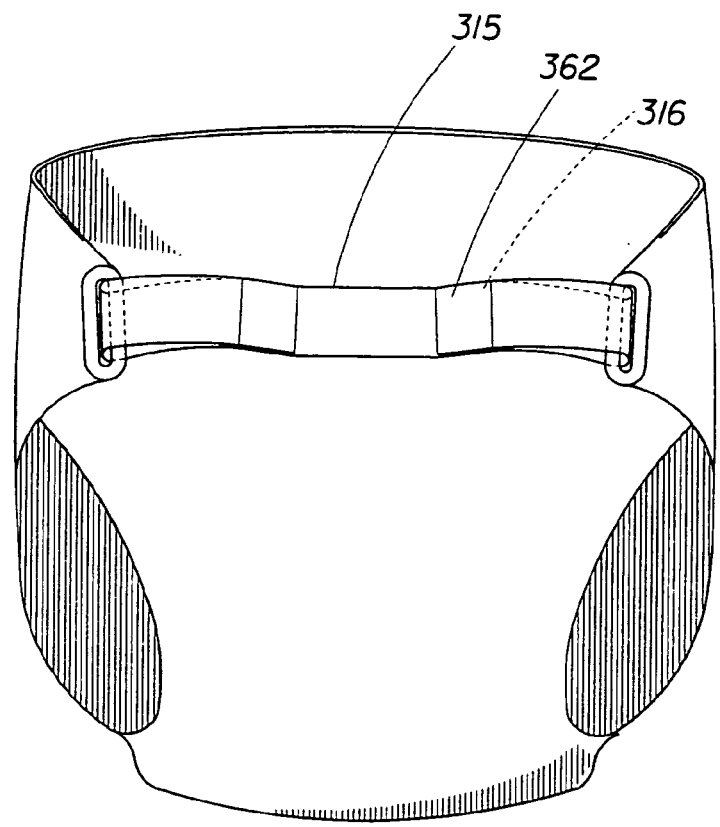
FIG. 24 is a perspective view of an absorbent article embodiment of the present invention.

Alternatively, as shown in FIG. 24, an adjustable fastening device 341 may include a strip 315 that has a fastening element 316 on the distal end 362 of the strip 315. In one embodiment, the strip or a portion of the article may also include a landing area to which the distal end 362 of the strip may attach. In this embodiment, the strip 315 may be fed through at least one slot member 344 and be folded back and attached to the strip 315 or the article via the fastening element 316. The distal end 362 of the strip may be attached to itself or to another portion of the article such as to the landing zone described above, to a backsheet, or another portion of the strip 315 or the article. For example, in FIG. 24, the strip 315 is folded back over itself and the distal end 362 of the strip 315 includes a fastener that attaches to a portion of the strip 315 and maintains the first waist region in contact with the second waist region. The fastening element 316 may include, for example, an adhesive, a cohesive, a mechanical fastener, a button, a snap, a magnet or any other fasteners known in the art, or another tab and slot fastener. Alternatively, the distal end 362 of the strip 315 may be fastened to another strip by tying the two distal ends 362 together, or the distal end of the strip may be fastened to itself by tying the distal end 362 of the strip 315 to the proximal end 360 of the strip 315.

Figure 25:
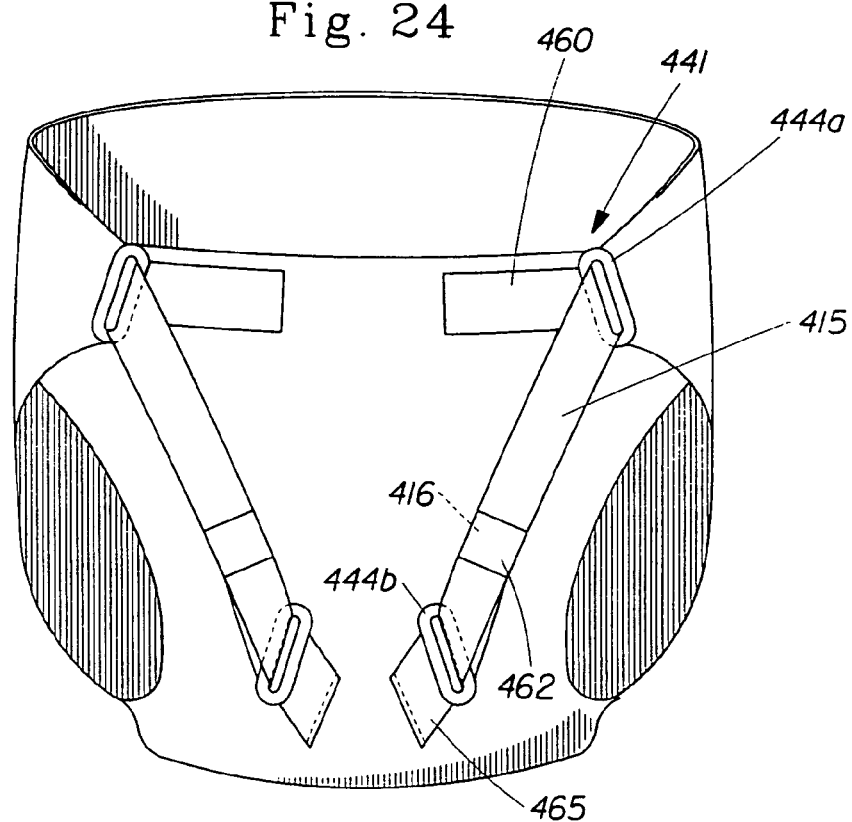
FIG. 25 is a perspective view of an absorbent article embodiment of the present invention.
Figure 26:
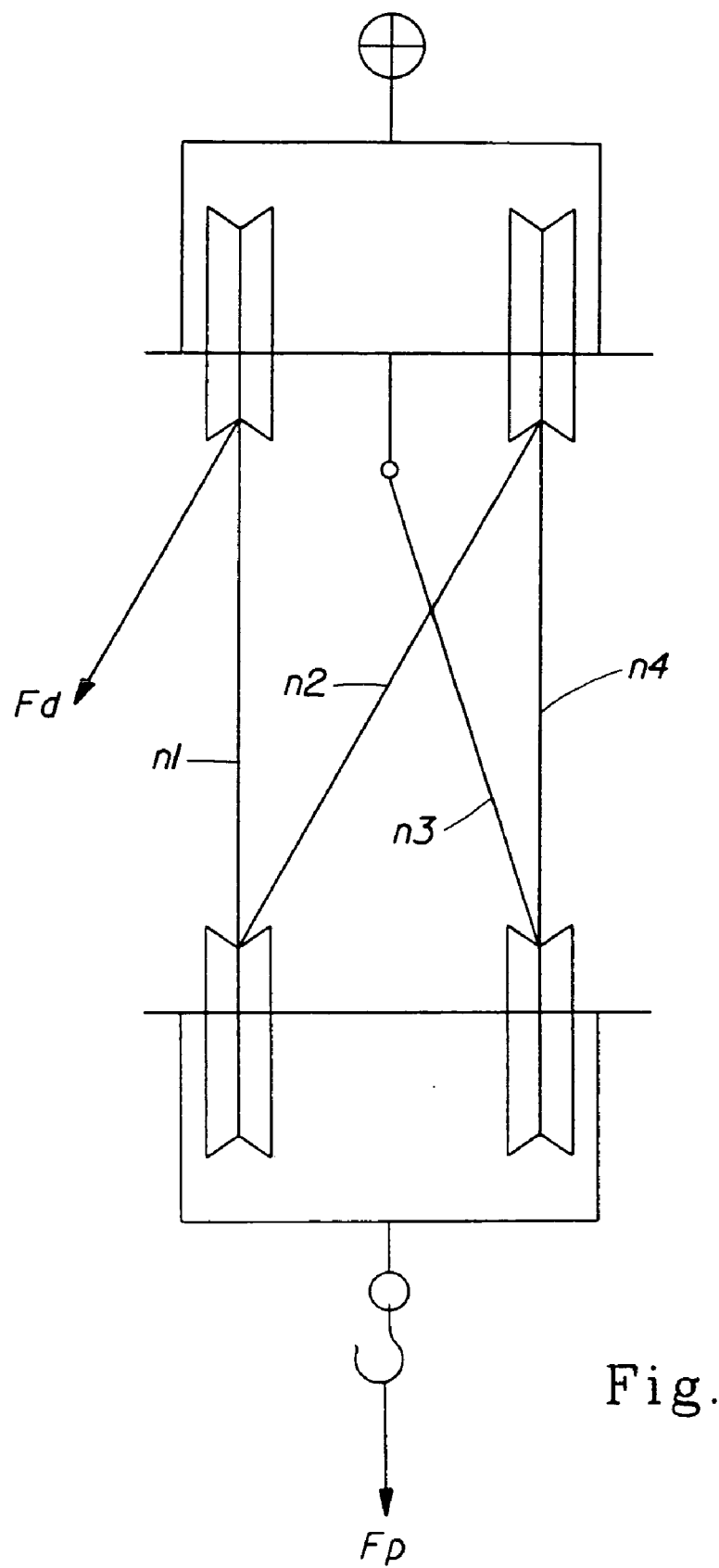
FIG. 26 is a side view of a pulley system.

An adjustable fastening device 441 including a strip 415 such as the one above may also be designed to limit the forces applied to the fastening element 416 by utilizing a "pulley" effect in which the forces that would be applied to the fastener may be distributed between the slot member and the fastener. For example, in the embodiment shown in FIG. 25, the strip 415 is attached to the backsheet of the diaper in the front waist region and is fed through slot members 444a and 444b and attached back to itself. In this embodiment, the force that is applied to the fastening element 416 at the distal end 462 of the strip 415 is a fraction of the force that is applied to the proximal end 460 of the strip 415, which can generally be expressed by the following formula: $Fd=(Vw \cdot Fp)/Vf=Fp/n$. A "pulley system" includes at least one pulley and at least two rope segments, i.e., n is greater than or equal to 2. An exemplary pulley system including four rope segments, i.e., n=4, is shown in FIG. 26 in order to illustrate the terms of the formula. The term Fp refers to the force applied to the fastener at the proximal end 460 of the strip 415; Fd refers to the force transferred to the distal end of the strip 415; Vp and Vd refer to the respective velocities of Fp and Fd, respectively; and n refers to the number of rope or strip 415 segments that are involved in the "pulley system." In an embodiment of an absorbent article such as a diaper, for example, the pulley may comprise a slot, a slit, a loop, and the like through which the "rope" may extend. The "rope" in this embodiment may include, for example, a strip member such as one or more strips, ropes, strings, elastic bands or strands, and the like. Alternatively, in various embodiments, such as the one shown in FIG. 25 in which the strip 415 segments diverge in various angles, the formulas listed above may not completely describe the precise load sharing, but the general principle of load sharing still applies. The formulas for various other pulley arrangements may be determined as known in the art from a standard mechanical engineering reference book such as Baumeister & Marks,"*The Standard Handbook For Mechanical Engineers*," Seventh Ed., McGraw Hill Book Co. (1967). The decrease in the force applied to the fastening element 416 enables the use of fasteners that do not have the strength required to independently hold for a given use. Thus, a softer fastener that may be more comfortable and less likely to mark, irritate or injure the skin of the wearer may be used. In addition, "pulley-type" systems that include more than two slot members may be used to further reduce the forces applied to the fastening element 416.

Figure 27:
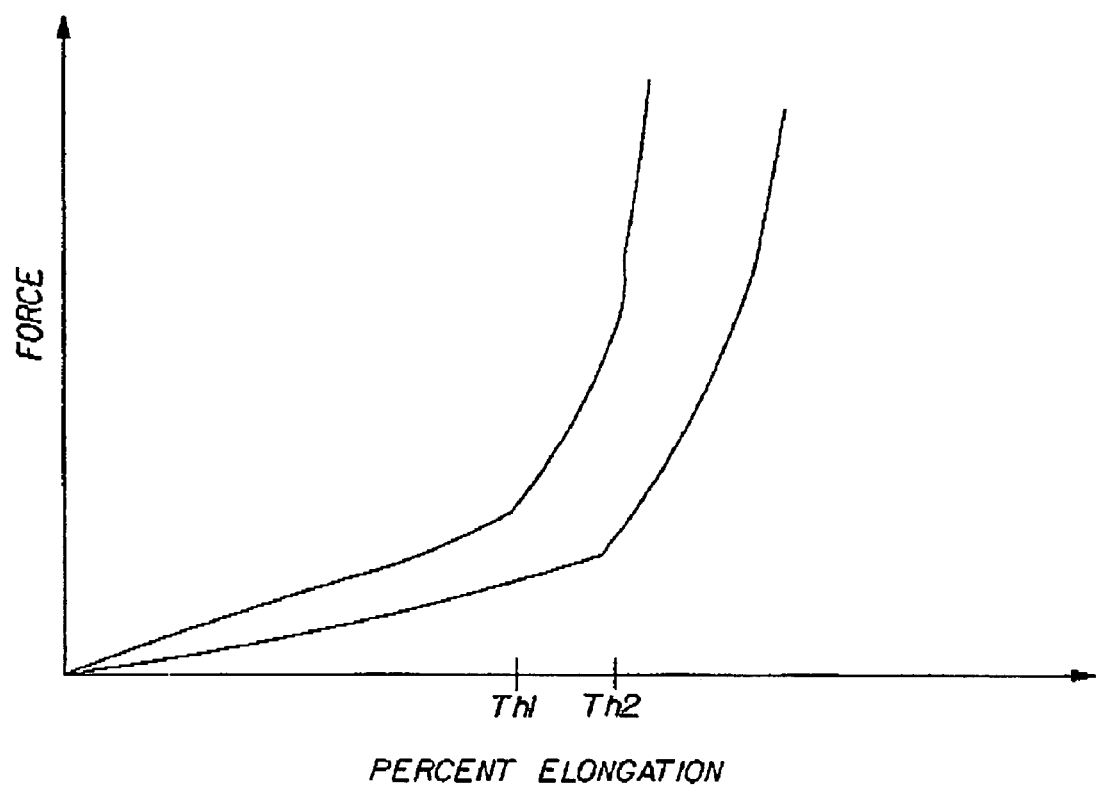
FIG. 27 is a graph of Force versus Percent Elongation for two exemplary materials.

In one aspect of this embodiment, the strip 415 may be elastic, elastomeric, extensible, etc. such that as a force is applied to the proximal end 460 of the strip 415 the strip is able to stretch. Alternatively, or in addition, the retaining material 465 attached to the slot member 444 may be elastic, elastomeric, extensible, etc. so that it may stretch in response to a change in dimension in order to keep the diaper fastened securely around the wearer. In these examples, the increase in the force applied to the fastening element 416 due to the stretch of the strip 415 or the retaining material 465 may be reduced by a pulley effect of a pulley-type fastening system. The extra length of elastic material involved in the pulley-type system may result in less relative strain being applied to the strip 415 or retaining material 465. FIG. 27, for example, shows a force versus percent elongation characteristic for two exemplary materials in which the slope of the force required to increase the elongation of the material is relatively low for an initial period and then substantially increases after a threshold percent elongation level such as Th1 or Th2. The action of the pulley effect of a pulley system may decrease the required relative elongation needed enough to keep the elongation less than the threshold level for that material. This results in a force even lower than would otherwise be accounted for by the pulley system's effect alone. This may substantially decrease the forces applied to the fastening element 416. Further, the pulley effect may allow the use of materials that, without the effect, would not be suitable for a particular product and/or application. For example, in a non-pulley system, a given strip 415 or retaining material 465 may need to provide a 50% to 200% stretch range, while the same material may only require about a 25% to 100% stretch range in order to fit the same dimension range in a pulley effect system having two rope or strip sections. This may, for example, allow the use of a material having a threshold percent elongation level of Th1 instead of a material having a threshold level of Th2. In some applications, it may also be desirable to have a higher elastic modulus in the strip 415 or in the retaining material 465 attached to the slot member. The modulus of the strip 415 and the retaining material 465 may be controlled as known in the art by varying the size, e.g., width or thickness, of the strip or retaining material, or by using different materials have various elastic moduli for the different components. This may, for example, allow the design of a fastening device 441 in which the relative positions of the various slot members are controlled or to vary the amount of the force applied to one area of the article over the other. In a diaper, for example, it may be desirable to direct most of the force to the back of the diaper and minimize the conforming forces over the top of the leg where skin marks or irritation may occur.

FIGS. 12 and 13 show alternative configurations of absorbent article embodiments of the present invention. In FIG. 12, the fastening device 41 is shown to include a tab member 42 and a slot member 44 located on opposite sides of the diaper 20 in the same waist region. This configuration provides one means for using the tab member 42 and the slot member 44 to fasten the diaper 20 in a disposal configuration. In such embodiments, either waist region can be folded inwardly and rolled toward the other waist region. The side panels 28 can then be wrapped around the folded and rolled portion of the diaper 20. The tab member 42 and the slot member 44 located in the same waist region can then be engaged to hold the diaper in a disposal configuration. An alternative embodiment of the diaper 20 with the fastening device 41 engaged in the disposal configuration is shown in FIG. 13. The diaper 20 of FIG. 13 includes a fastening device 41 having two slot members 44 which are engageable. (Other embodiments may include one or more tab members 42 having slots 46 so as to allow for alternative attachment and disposal.) If the slot member 44 includes a grip tab 69, the interlocked slots can be further secured by passing the grip tab 69 through the slot 46 of the opposing slot member 44. Of course, the diaper 20 of the present invention can have a disposal fastening device in addition to the fastening system 40. For example, the diaper 20 may include a tape tab, hook and loop, tab and slot or other mechanical fasteners specifically positioned to be useful for disposal. Alternatively, absorbent articles may include primary fastening means such as tapes, hook and loop fasteners or any other known fasteners and use the tab and slot fastening device 41 of the present invention as the disposal means.

Figure 15:
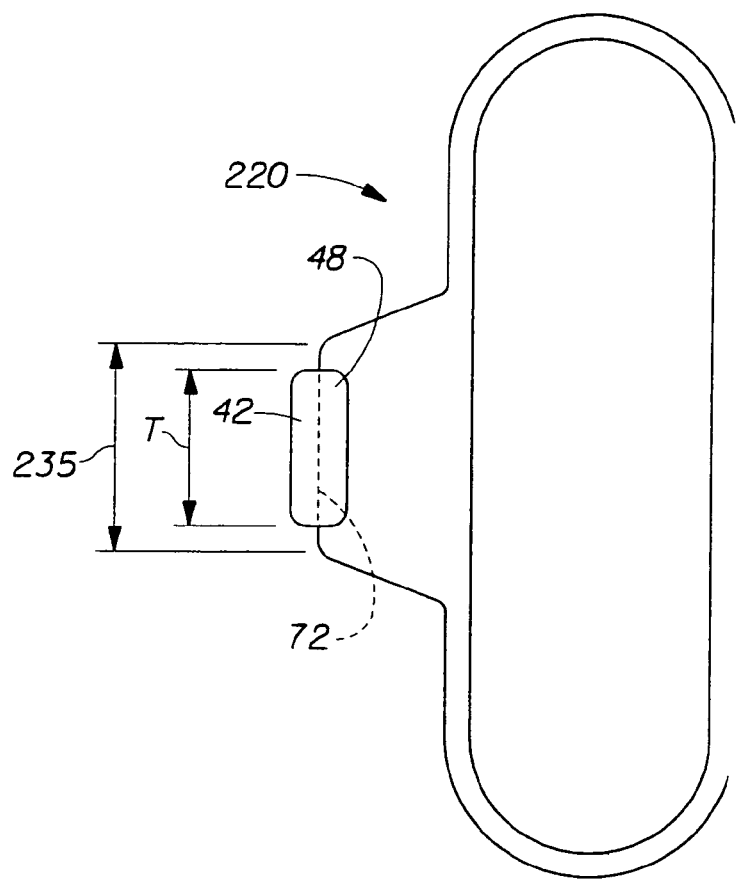
FIG. 15 is a plan view of a sanitary napkin embodiment including the fastening device of the present invention.
Figure 16:
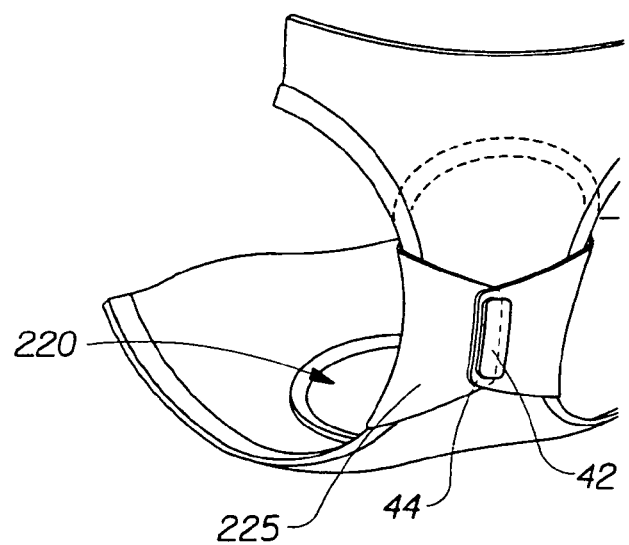
FIG. 16 is a perspective view of a sanitary napkin embodiment of the present invention shown in a fastened configuration.

FIGS. 15 and 16 show a sanitary napkin embodying the fastening device 41 of the present invention. The fastening device 41 is used to fasten the wings 225 of a sanitary napkin 220 about the wearer's panty 230. Fastening the wings 225 of the sanitary napkin about the wearer's undergarment helps ensure that the sanitary napkin 220 will stay in place while in use and provides a means for reducing the likelihood that the panty 230 will be soiled if the core of the napkin 220 should leak. Although the fastening device 41 is shown in the figures as the primary fastening device, the fastening device 41 of the present invention can be used in conjunction with other means for securing the napkin 220 to the panties 230 or around the panties 220 such as adhesives, mechanical fasteners, buttons, snaps, friction, static and/or any other means known in the art. The fastening device 41 may also be used to fasten the sanitary napkin 220 to other devices such as belts, other sanitary guards, or the wearer's undergarments, or may be used as a means for wrapping the napkin in a disposal configuration. Examples of sanitary napkins with which the fastening system 40 of the present invention may be used are described in detail in U.S. Pat. No. 5,267,992 entitled "Shaped Sanitary Napkin With Flaps" which issued to Van Tilburg on Dec. 7, 1993 and U.S. Pat. No. 5,389,094 entitled "Absorbent Article Having Flaps and Zones of Differential Extensibility" which issued to Lavash et al. on Feb. 14, 1995. Both of these patents are hereby incorporated by reference herein.

In one preferred embodiment, as shown in FIGS. 15 and 16, the tab member 42 of the fastening device 41 is joined to one of the wings 225 of the sanitary napkin 220 and the slot member 44 is joined to the other wing. The tab member 42 is joined to the wing 225 along a line of attachment 72 such that the lip portion 48 of the tab member 42 extends laterally inwardly over at least a portion of the wing 225. The slot member 44 is shown as an integral part of the wing 225, however, the slot member may be a separate element joined to the wing 225. The wing 225 of the sanitary napkin 220 has a longitudinal dimension 235. Preferably, the length T of the tab member 42 is greater than or equal to 50% of the longitudinal dimension 235 of the wing 225. It is also preferred that the line of attachment 72 between the tab member 42 and the wing 225 be greater than or equal to 25% of the length T of the tab member 42. In order to increase the stability of the tab member 42 and to distribute the forces which act on the fastening device 41 when it is fastened, it is preferred that the line of attachment 72 be greater than or equal to 50% of the length T of the tab member 42. In an especially preferred embodiment, the line of attachment 72 is at least 75% of the length T of the tab member 42. In any case, the line of attachment can be continuous or intermittent so long as the forces acting on the fastener when fastened are distributed across at least 25% of the longitudinal dimension 235 of the wing 225.

Figure 17:
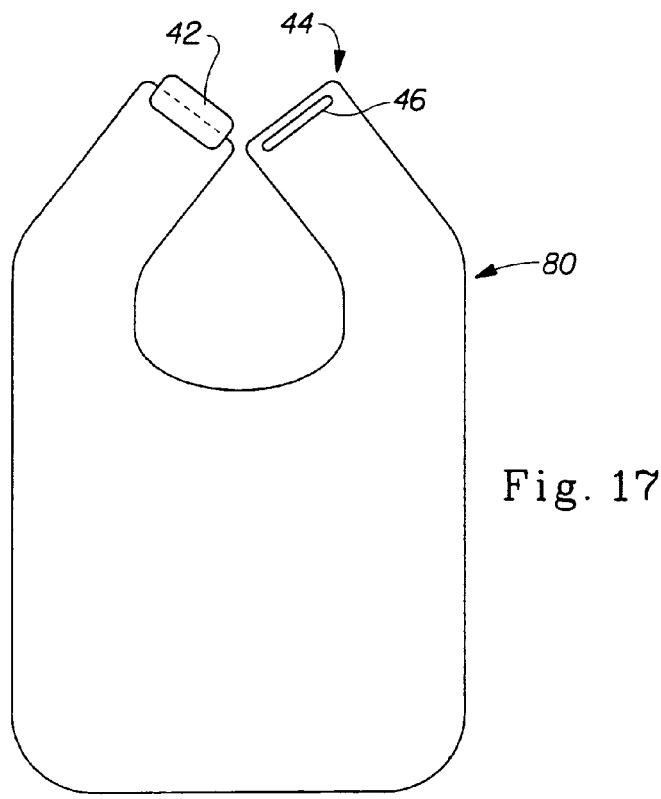
FIG. 17 is a plan view of a bib embodiment including the fastening device of the present invention.

FIG. 17 is one example of a bib 80 embodiment including the fastening device 41 of the present invention. The tab member 42 and the slot member 44 are disposed such that they can fasten the bib 80 about the neck of the wearer. Alternative embodiments are contemplated wherein the fastening device 41 includes multiple tab members 42 and /or slot members 44 to provide adjustability. The fastening device 41 may also provide a means for disposal. The tab member 42, the slot member 44 or both may be integral with the bib 80 or separate elements joined thereto. Further, the tab and slot fastening device 41 may be the primary fastening system or may be a secondary fastening system.

Figure 18:
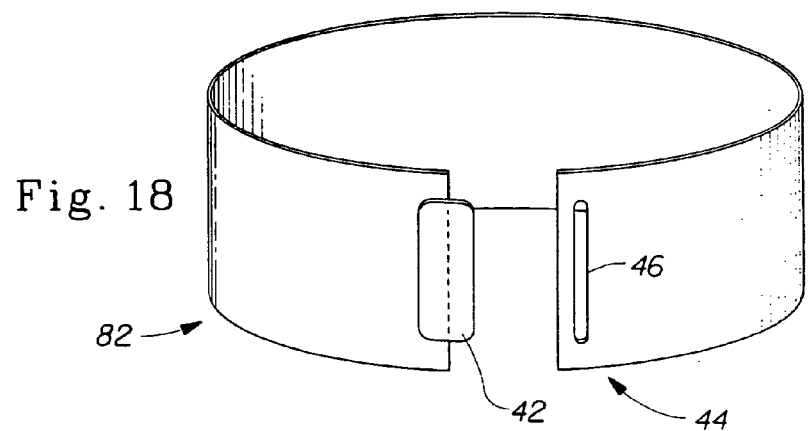
FIG. 18 is a plan view of a wrap embodiment including the fastening device of the present invention.

FIG. 18 is one example of a wrap 82 embodiment including the fastening device 41 of the present invention. The tab member 42 and the slot member 44 are disposed such that they can join at least a portion of the wrap adjacent one end of the wrap 82 to another portion of the wrap 82. Alternative embodiments are contemplated wherein the fastening device 41 includes multiple tab members 42 and /or slot members 44 to provide adjustability. The fastening device 41 may also provide a means for disposal. The tab member 42, the slot member 44 or both may be integral with the wrap 82 or separate elements permanently or temporarily joined thereto. Further, the tab and slot fastening device 41 may be the primary fastening system or may be a secondary fastening system for the wrap 82.

While particular embodiments of the present invention have been illustrated and described, it would be obvious to those skilled in the art that various other changes and modifications can be made without departing from the spirit and scope of the invention. The use of a fastener of the present invention, for example, may include a fastener for a belt-type absorbent article in which the belt wraps around the wearer and connects one waist region to itself, a fastener that connects one waist region to the other waist region, a disposal fastening device, or any combination thereof. A belt-type fastener may comprise a separate belt that may be joined to the article through a fastener of the present invention, slits, loops, slots, buckles, ties, or any fastener known in the art. Alternatively, a belt can be joined to a portion of the article such as the front or rear waist region and may connect that portion of the article to the wearer and/or to another portion of the article through a fastener of the present invention, slits, loops, slots, buckles, ties, or any fastener known in the art. The fastener of the present invention may also include either a primary fastener, a secondary fastener, or both in a fastening system such as the one disclosed in U.S. Pat. No. 4,699,622 entitled "Disposable Diaper Having An Improved Side Closure," issued to John W. Toussaint et al. on Oct. 13, 1987, which is incorporated by reference herein. In addition, a fastener of the present invention may also be used in an absorbent article that has separable components in order to hold or attach the separable component(s) to some part of the assembly. The separable component(s) may be, for example, an absorbent core and a liner, or a set of suspenders or other garment from which the absorbent article is supported. It should also be clear that the fasteners of the present invention may be readily adapted to any of the product forms described above. The present invention is therefore intended to cover in the appended claims all such changes and modifications that are within the scope of this invention.

All documents cited in the Detailed Description of the Invention are, in relevant part, incorporated by reference herein; the citation of any document is not to be construed as an admission that it is prior art with respect to the present invention. To the extent that any meaning or definition of the term in this written document conflicts with any meaning or definition of the term in a document incorporated by reference, the meaning or definition assigned to the term in this written document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An absorbent article having a first waist region, a second waist region opposed to the first waist region and a crotch region located between the first waist region and the second waist region, a pair of longitudinal edges and a pair of end edges, the absorbent article comprising:
   a topsheet:
   a backsheet joined with the topsheet;
      an absorbent core positioned between the topsheet and the backsheet, the absorbent core including a pair of side edges and a pair of waist edges; and
      a fastening system for joining at least a portion of the first waist region with at least a portion of the second waist region to provide lateral tension therebetween the fastening system including:
         a slot member disposed on the absorbent article, the slot member having an inboard portion, an outboard portion and a slot, the inboard portion located laterally inboard of the outboard portion and the slot located between the inboard portion and the outboard portion; and
         a tab member disposed on the absorbent article, said tab member having a proximal edge and a distal edge, the proximal edge located laterally inward from the distal edge, wherein the tab member distal edge and proximal edge are passed througb the slot such that a portion of the proximal edge of the tab member overlaps the outboard portion of the slot member so as to fasten a portion of the first waist region with at least a portion of the second waist region.

2. The absorbent article of claim 1 wherein said the tab member is joined to the absorbent article along a line of attachment extending at least about 25 percent of the length of the tab member.

3. The absorbent article of claim 1 wherein the line of attachment is located between the proximal edge and the distal edge of the tab member.

4. The absorbent article of claim 1 wherein the line of attachment is located adjacent the distal edge of the tab member.

5. The absorbent article of claim 1 wherein the line of attachment extends at least about 50 percent of the length of the tab member.

6. The absorbent article of claim 1 wherein the line of attachment extends at least about 75 percent of the length of the tab member.

7. The absorbent article of claim 1 wherein the line of attachment extends about the full length of the tab member.

8. The absorbent article of claim 1 wherein the line of attachment is non-linear.

9. The absorbent article of claim 1 wherein the distal edge of the tab member is non-linear.

10. The absorbent article of claim 1 wherein the tab member further includes a first longitudinal end, a second longitudinal end and a central region, said first longitudinal end being displaced laterally from the central region.

11. The absorbent article of claim 10 said second longitudinal end being displaced laterally from the central region.

12. The absorbent article of claim 1 wherein the slot member is integral with the absorbent article.

13. The absorbent article of claim 1 wherein the slot member includes two or more slots.

14. The absorbent article of claim 13 wherein the slots are spaced longitudinally apart from each other.

15. The absorbent article of claim 13 wherein the slots are spaced laterally apart from each other.

16. The absorbent article of claim 1 wherein the slot member further includes an outboard edge and an inboard edge, the outboard edge being non-linear.

17. The absorbent article of claim 1 wherein the slot of the slot member is non-linear.

18. The absorbent article of claim 1 wherein the slot member further includes a first longitudinal end, a second longitudinal end and a central region, the first longitudinal end being displaced laterally from the central region.

19. The absorbent article of claim 18 said second longitudinal end being displaced laterally from the central region.

20. The absorbent article of claim 1 including two or more slot members.

* * * * *